(12) United States Patent
Cain

(10) Patent No.: US 9,597,195 B2
(45) Date of Patent: Mar. 21, 2017

(54) EXPANDABLE INTERVERTEBRAL IMPLANT

(71) Applicant: DePuy Synthes Products, Inc., Raynham, MA (US)

(72) Inventor: Christopher Marden John Cain, Aurora, CO (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/685,402

(22) Filed: Apr. 13, 2015

(65) Prior Publication Data
US 2015/0216672 A1     Aug. 6, 2015

Related U.S. Application Data

(63) Continuation of application No. 14/565,611, filed on Dec. 10, 2014, which is a continuation of application (Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/442* (2013.01); *A61F 2/447* (2013.01); *A61F 2/4611* (2013.01); *A61F 2002/2835* (2013.01); *A61F 2002/305* (2013.01); *A61F 2002/3052* (2013.01); *A61F 2002/3055* (2013.01);
(Continued)

(58) Field of Classification Search
CPC .. A61F 2/4611; A61F 2002/448; A61F 2/447; A61F 2002/30579; A61F 2002/30601; A61F 2002/4415
See application file for complete search history.

(56) References Cited

U.S. PATENT DOCUMENTS

| 4,349,921 A | 9/1982 | Kuntz |
| 4,863,476 A | 9/1989 | Shepperd |

(Continued)

FOREIGN PATENT DOCUMENTS

| CN | 101909548 A | 12/2010 |
| DE | 4012622 | 7/1997 |

(Continued)

OTHER PUBLICATIONS

U.S. Appl. No. 14/685,358, filed Mar. 13, 2015, Marden et al.
(Continued)

*Primary Examiner* — Anu Ramana
(74) *Attorney, Agent, or Firm* — Baker & Hostetler LLP

(57) ABSTRACT

An expandable intervertebral implant is provided for insertion into an intervertebral space defined by adjacent vertebrae. The expandable intervertebral implant includes a pair of outer sleeve portions and an inner core disposed between the outer sleeve portions. Movement of the inner core relative to the outer sleeve portions causes the outers sleeve portions to deflect away from each other, thereby engaging the expandable intervertebral implant with the vertebrae and adjusting the height of the intervertebral space.

17 Claims, 24 Drawing Sheets

Related U.S. Application Data

No. 12/936,466, filed as application No. PCT/US2009/039501 on Apr. 3, 2009, now Pat. No. 8,936,641.

(60) Provisional application No. 61/042,724, filed on Apr. 5, 2008.

(51) Int. Cl.
    *A61F 2/28*     (2006.01)
    *A61F 2/30*     (2006.01)

(52) U.S. Cl.
    CPC ............ *A61F 2002/30405* (2013.01); *A61F 2002/30462* (2013.01); *A61F 2002/30471* (2013.01); *A61F 2002/30495* (2013.01); *A61F 2002/30537* (2013.01); *A61F 2002/30538* (2013.01); *A61F 2002/30551* (2013.01); *A61F 2002/30579* (2013.01); *A61F 2002/30601* (2013.01); *A61F 2002/30616* (2013.01); *A61F 2002/30841* (2013.01); *A61F 2002/30884* (2013.01); *A61F 2002/443* (2013.01); *A61F 2002/448* (2013.01); *A61F 2002/4415* (2013.01); *A61F 2002/4485* (2013.01); *A61F 2002/4627* (2013.01); *A61F 2002/4628* (2013.01); *A61F 2220/0025* (2013.01); *A61F 2220/0075* (2013.01); *A61F 2220/0091* (2013.01); *A61F 2250/0006* (2013.01); *A61F 2310/00023* (2013.01)

(56) References Cited

U.S. PATENT DOCUMENTS

| | | | |
|---|---|---|---|
| 5,059,193 A | 10/1991 | Kuslich | |
| 5,290,312 A | 3/1994 | Kojimoto et al. | |
| 5,344,252 A | 9/1994 | Kakimoto | |
| 5,370,697 A | 12/1994 | Baumgartner | |
| 5,390,683 A | 2/1995 | Pisharodi | |
| 5,443,514 A | 8/1995 | Steffee | |
| 5,522,899 A | 6/1996 | Michelson | |
| 5,534,029 A | 7/1996 | Shima | |
| 5,554,191 A | 9/1996 | Lahille et al. | |
| 5,609,635 A | 3/1997 | Michelson | |
| 5,653,763 A | 8/1997 | Errico | |
| 5,658,335 A | 8/1997 | Allen | |
| 5,665,122 A | 9/1997 | Kambin | |
| 5,697,977 A | 12/1997 | Pisharodi | |
| 5,716,415 A | 2/1998 | Steffee | |
| 5,772,661 A | 6/1998 | Michelson | |
| 5,782,832 A | 7/1998 | Larsen et al. | |
| 5,860,973 A | 1/1999 | Michelson | |
| 5,865,848 A | 2/1999 | Baker | |
| 5,888,224 A | 3/1999 | Beckers et al. | |
| 5,893,889 A | 4/1999 | Harrington | |
| 5,893,890 A | 4/1999 | Pisharodi | |
| 5,980,522 A | 11/1999 | Koros et al. | |
| 6,039,761 A | 3/2000 | Li | |
| 6,045,579 A | 4/2000 | Hochshuler | |
| 6,102,950 A | 8/2000 | Vaccaro | |
| 6,106,557 A | 8/2000 | Robioneck et al. | |
| 6,117,174 A | 9/2000 | Nolan | |
| 6,127,597 A | 10/2000 | Beyar et al. | |
| 6,129,763 A | 10/2000 | Chauvin et al. | |
| 6,146,387 A | 11/2000 | Trott et al. | |
| 6,176,882 B1 | 1/2001 | Biedermann et al. | |
| 6,179,794 B1 | 1/2001 | Burras | |
| 6,179,873 B1 | 1/2001 | Zientek | |
| 6,183,517 B1 | 2/2001 | Suddaby | |
| 6,193,757 B1 | 2/2001 | Foley et al. | |
| 6,296,647 B1 | 10/2001 | Robioneck et al. | |
| 6,302,914 B1 | 10/2001 | Michelson | |
| 6,332,895 B1 | 12/2001 | Suddaby | |
| 6,368,351 B1 | 4/2002 | Glenn | |
| 6,375,682 B1 | 4/2002 | Fleischmann et al. | |
| 6,387,130 B1 | 5/2002 | Stone | |
| 6,409,766 B1 | 6/2002 | Brett | |
| 6,419,705 B1 | 7/2002 | Erickson | |
| 6,419,706 B1 | 7/2002 | Graf | |
| 6,436,140 B1 | 8/2002 | Liu et al. | |
| 6,454,806 B1 | 9/2002 | Cohen et al. | |
| 6,454,807 B1 | 9/2002 | Jackson | |
| 6,488,710 B2 | 12/2002 | Besselink | |
| 6,527,804 B1 | 3/2003 | Gauchet et al. | |
| 6,558,424 B2 | 5/2003 | Thalgott | |
| 6,562,074 B2 | 5/2003 | Gerbec et al. | |
| 6,582,468 B1 | 6/2003 | Gauchet | |
| 6,610,094 B2 | 8/2003 | Husson | |
| 6,641,614 B1 | 11/2003 | Wagner et al. | |
| 6,648,917 B2 | 11/2003 | Gerbec et al. | |
| 6,676,665 B2 | 1/2004 | Foley et al. | |
| 6,706,070 B1 | 3/2004 | Wagner et al. | |
| 6,719,796 B2 | 4/2004 | Cohen et al. | |
| 6,723,126 B1 | 4/2004 | Berry | |
| 6,733,532 B1 | 5/2004 | Gauchet et al. | |
| 6,743,255 B2 | 6/2004 | Ferree | |
| 6,773,460 B2 * | 8/2004 | Jackson ................ | A61F 2/4455 623/17.11 |
| 6,805,714 B2 | 10/2004 | Sutcliffe | |
| 6,855,167 B2 | 2/2005 | Shimp | |
| 6,863,673 B2 | 3/2005 | Gerbec et al. | |
| 6,893,464 B2 | 5/2005 | Kiester | |
| 6,953,477 B2 | 10/2005 | Berry | |
| 6,955,691 B2 | 10/2005 | Chae et al. | |
| 6,969,404 B2 | 11/2005 | Ferree | |
| 6,969,405 B2 | 11/2005 | Suddaby | |
| 7,018,412 B2 | 3/2006 | Ferreira et al. | |
| 7,018,416 B2 | 3/2006 | Hanson et al. | |
| 7,037,339 B2 | 5/2006 | Houfburg et al. | |
| 7,083,650 B2 | 8/2006 | Moskowitz et al. | |
| 7,094,257 B2 | 8/2006 | Mujwid et al. | |
| 7,211,112 B2 | 5/2007 | Baynham et al. | |
| 7,217,293 B2 | 5/2007 | Branch | |
| 7,220,280 B2 | 5/2007 | Kast et al. | |
| 7,223,292 B2 | 5/2007 | Messerli et al. | |
| 7,226,483 B2 | 6/2007 | Gerber et al. | |
| 7,235,101 B2 | 6/2007 | Berry et al. | |
| 7,326,248 B2 | 2/2008 | Michelson | |
| 7,503,933 B2 | 3/2009 | Michelson | |
| 7,507,241 B2 | 3/2009 | Levy et al. | |
| 7,569,074 B2 | 8/2009 | Eiserman et al. | |
| 7,618,458 B2 | 11/2009 | Biedermann et al. | |
| 7,621,950 B1 | 11/2009 | Globerman et al. | |
| 7,621,960 B2 | 11/2009 | Boyd et al. | |
| 7,691,147 B2 | 4/2010 | Gutlin et al. | |
| 7,703,727 B2 | 4/2010 | Selness | |
| 7,722,612 B2 | 5/2010 | Sala et al. | |
| 7,722,674 B1 | 5/2010 | Grotz | |
| 7,749,270 B2 | 7/2010 | Peterman | |
| 7,771,473 B2 | 8/2010 | Thramann | |
| 7,785,368 B2 | 8/2010 | Schaller | |
| 7,789,914 B2 | 9/2010 | Michelson | |
| 7,819,921 B2 | 10/2010 | Grotz | |
| 7,824,445 B2 | 11/2010 | Biro et al. | |
| 7,837,734 B2 | 11/2010 | Zucherman et al. | |
| 7,846,206 B2 | 12/2010 | Oglaza et al. | |
| 7,850,733 B2 * | 12/2010 | Baynham ................ | A61F 2/447 623/17.11 |
| 7,854,766 B2 | 12/2010 | Moskowitz et al. | |
| 7,874,980 B2 | 1/2011 | Sonnenschein et al. | |
| 7,879,098 B1 | 2/2011 | Simmons | |
| 7,887,589 B2 | 2/2011 | Glenn et al. | |
| 7,909,870 B2 | 3/2011 | Kraus | |
| 7,922,729 B2 | 4/2011 | Michelson | |
| 7,951,199 B2 | 5/2011 | Miller | |
| 7,985,231 B2 | 7/2011 | Sankaran | |
| 7,993,403 B2 | 8/2011 | Foley et al. | |
| 8,021,424 B2 | 9/2011 | Beger et al. | |
| 8,021,426 B2 | 9/2011 | Segal et al. | |
| 8,025,697 B2 | 9/2011 | McClellan et al. | |
| 8,034,109 B2 | 10/2011 | Zwirkoski | |
| 8,043,381 B2 | 10/2011 | Hestad et al. | |
| 8,062,375 B2 | 11/2011 | Glerum et al. | |

(56) References Cited

U.S. PATENT DOCUMENTS

| | | |
|---|---|---|
| 8,075,621 B2 | 12/2011 | Michelson |
| 8,177,812 B2 | 5/2012 | Sankaran |
| 8,192,495 B2 | 6/2012 | Simpson et al. |
| 8,221,501 B2 | 7/2012 | Eiserman et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,603,170 B2 | 12/2013 | Cipoletti et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,936,641 B2 | 1/2015 | Cain |
| 8,940,052 B2 | 1/2015 | Lechmann et al. |
| 9,095,446 B2 | 8/2015 | Landry et al. |
| 9,095,447 B2 | 8/2015 | Barreiro et al. |
| 2002/0068976 A1 | 6/2002 | Jackson |
| 2002/0068977 A1 | 6/2002 | Jackson |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0140207 A1 | 6/2008 | Olmos |
| 2008/0147193 A1 | 6/2008 | Matthis et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0222096 A1 | 9/2009 | Trieu |

(56) References Cited

U.S. PATENT DOCUMENTS

| | | |
|---|---|---|
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0197403 A1 | 8/2012 | Merves |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0094812 A1 | 4/2015 | Cain |

FOREIGN PATENT DOCUMENTS

| | | |
|---|---|---|
| DE | 202008001079 | 3/2008 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2874814 | 3/2006 |
| JP | 2003-526457 | 9/2003 |
| JP | 2006-516456 | 7/2006 |
| JP | 2011-509766 A | 3/2011 |
| WO | WO 95/31158 | 11/1995 |
| WO | WO 97/00054 | 1/1997 |
| WO | WO 00/12033 | 3/2000 |
| WO | WO 00/74605 | 12/2000 |
| WO | WO 01/01895 | 1/2001 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/009107 | 1/2007 |
| WO | WO 2007/028098 | 3/2007 |
| WO | WO 2007/048012 | 4/2007 |
| WO | WO 2008/044057 | 4/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |

OTHER PUBLICATIONS

U.S. Appl. No. 14/640,220, filed Mar. 6, 2015, Marden.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.

(56) References Cited

OTHER PUBLICATIONS

Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Non-Final Rejection dated Oct. 7, 2015 issued in U.S. Appl. No. 14/640,220, 18 pages.
Non-Final Rejection dated Oct. 22, 2015 issued in U.S. Appl. No. 14/685,358, 13 pages.
Final Rejection dated Feb. 25, 2016 issued in U.S. Appl. No. 14/685,358, 13 pages.
Non-Final Rejection dated Mar. 4, 2016 issued in U.S. Appl. No. 14/988,501, 12 pages.
Non-Final Rejection dated Jul. 1, 2015 issued in U.S. Appl. No. 14/565,611, 17 pages.

\* cited by examiner

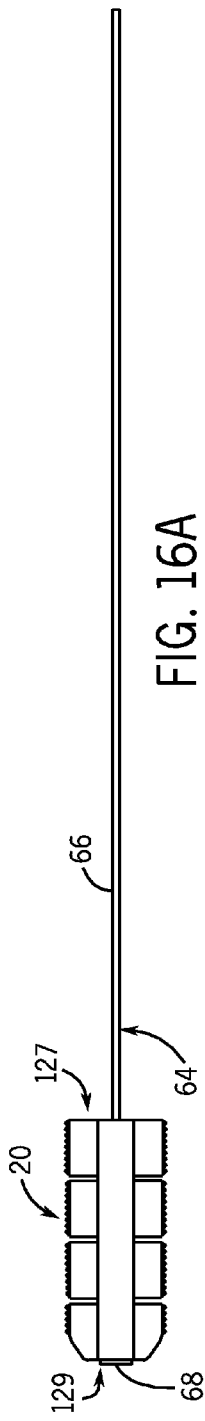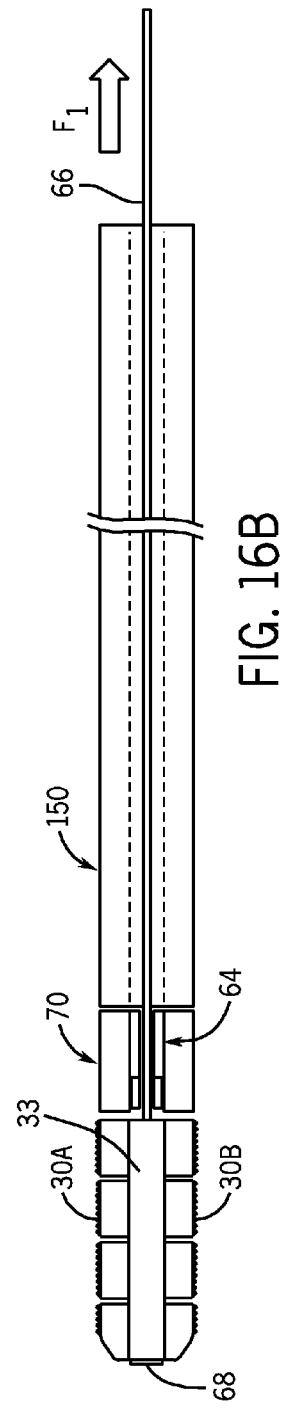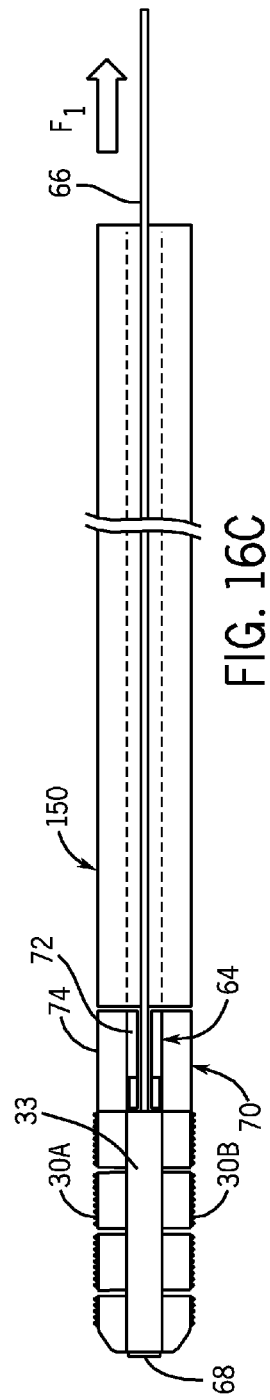

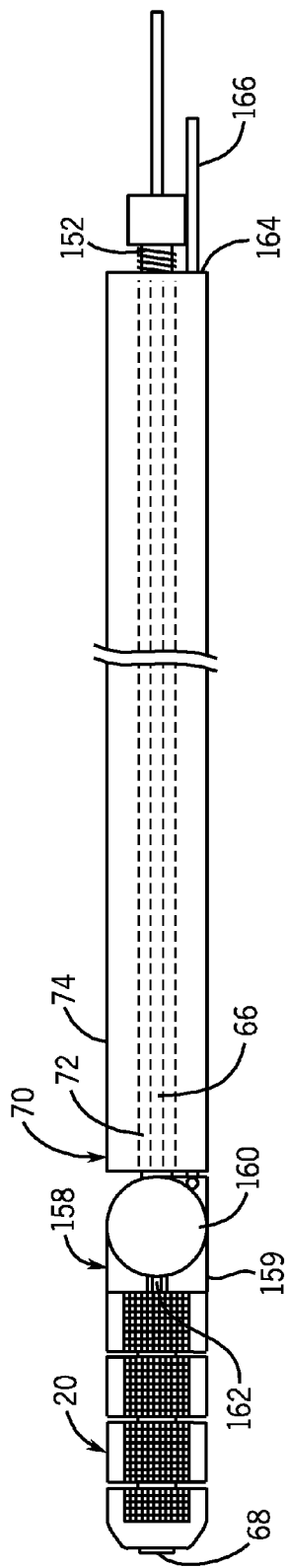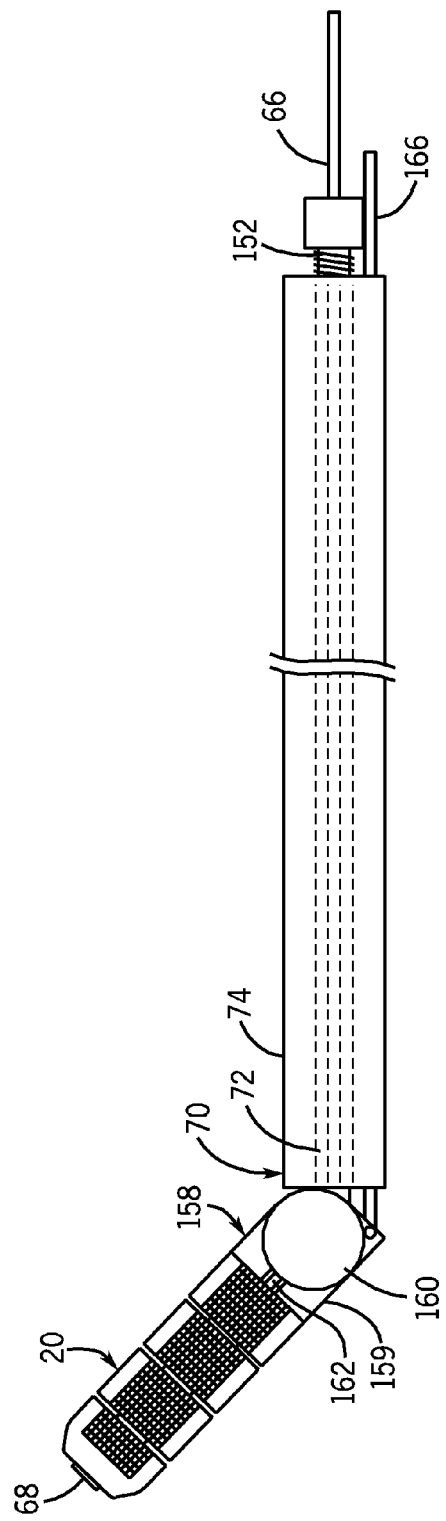
FIG. 18A
FIG. 18B

EXPANDABLE INTERVERTEBRAL IMPLANT

CROSS-REFERENCE TO RELATED APPLICATIONS

This is a continuation application of U.S. patent application Ser. No. 14/565,611 filed Dec. 10, 2014, which is a continuation application of U.S. patent application Ser. No. 12/936,466 filed Oct. 5, 2010, which is a National Stage of International Application Serial No. PCT/US2009/039501, filed Apr. 3, 2009, which claims the benefit of U.S. Provisional Application Ser. No. 61/042,724, filed on Apr. 5, 2008, the disclosure of each of which is hereby incorporated by reference as if set forth in its entirety herein.

FIELD OF THE INVENTION

This disclosure relates generally to intervertebral implants, and in particular relates to an intervertebral implant that can expand to create a desired spacing and/or angular orientation of adjacent vertebrae.

BACKGROUND OF THE INVENTION

Degenerative disc disease or degeneration of a vertebral body often results in a loss of disc height, which in turn can cause facet and nerve impingement, among other things. One standard of care is to replace the damaged intervertebral disc with an intervertebral implant or a damaged portion or an entire vertebral body with an intervertebral implant.

Thus, an intervertebral implant may be inserted into the intervertebral disc space of two adjacent vertebral bodies or into the space created by removal of portions of, or the entire, vertebral body after removal of damaged portions of the spine. Preferably, the intervertebral implant restores the spine, as much as possible, to a natural state. That is, the implant preferably restores the original height of the intervertebral disc and thus the original distance between the two adjacent vertebral bodies or vertebral bodies in various levels of the spine. These implants are sized and shaped to fill at least the physiological height between the vertebral bodies and are inserted through a relatively narrow and small incision with nerves and vascular structure proximate sides of the incision. Accordingly, it is advantageous to develop an implant that may be inserted in a reduced size or configuration and expanded when positioned between the vertebrae to minimize the required incision and limit the potential for the implant to contact the neural and vascular structure during implantation.

It is desirable to construct an intervertebral implant that restores the spine to its natural state, is relatively compact during insertion and may be expanded when positioned between adjacent vertebrae. It is also desirable to construct an expandable intervertebral implant that may be inserted and expanded utilizing the same instrument.

BRIEF SUMMARY OF THE INVENTION

The following Summary is provided to introduce a selection of concepts in a simplified form that are further described below in the Detailed Description of Illustrative Embodiments. This Summary is not intended to identify key features or essential features of the invention, nor is it intended to be used to limit the scope of the invention. Reference is made to the claims for that purpose.

Certain embodiments are directed to an expandable intervertebral implant for insertion into an intervertebral disc space and expandable from an initial position to an expanded position. The expandable intervertebral implant includes a linkage that includes a plurality of links connected in a longitudinal direction. Each link includes an outer sleeve having a first outer sleeve portion and a second outer sleeve portion that is movable with respect to the first outer sleeve portion. The second outer sleeve portion defines a first engagement surface that is sloped with respect to the longitudinal direction. Each link further includes an inner core disposed between the first and second outer sleeve portions. The inner core defines a second engagement surface that is sloped with respect to the longitudinal direction, wherein the second engagement surface abuts the first engagement surface. Relative movement between the inner core and the second outer sleeve portion along the longitudinal direction causes the first engagement surface to ride along the second engagement surface, thereby causing the second outer sleeve portion to deflect away from the first outer sleeve portion in a direction substantially perpendicular to the longitudinal direction.

Additional features and advantages will be made apparent from the following detailed description of illustrative embodiments with reference to the accompanying drawings.

BRIEF DESCRIPTION OF THE SEVERAL VIEWS OF THE DRAWINGS

The foregoing summary, as well as the following detailed description, is better understood when read in conjunction with the appended drawings. There is shown in the drawings example embodiments, in which like reference numerals correspond to like reference numerals throughout. The expandable intervertebral implant and related methods are not limited to the specific embodiments and methods disclosed, and reference is made to the claims for that purpose.

FIG. 16A is a side elevation view of an expandable intervertebral implant coupled to a biasing member of an insertion device in accordance with one embodiment;

FIG. 16B is a side elevation view of the expandable intervertebral implant illustrated in FIG. 16A, but with the biasing member coupled to additional components of the insertion device, wherein the insertion device is illustrated in a disengaged position;

FIG. 16C is a side elevation view of the expandable intervertebral implant as illustrated in FIG. 16B, but showing the insertion device in an engaged position;

FIG. 18A is a top plan view of an expandable intervertebral implant coupled to an angulated insertion device constructed in accordance with an alternative embodiment;

FIG. 18B is a top plan view of the expandable intervertebral implant coupled to the angulated insertion device illustrated in FIG. 18A, showing the insertion device in an angulated position;

DETAILED DESCRIPTION OF THE INVENTION

Figure 1A:
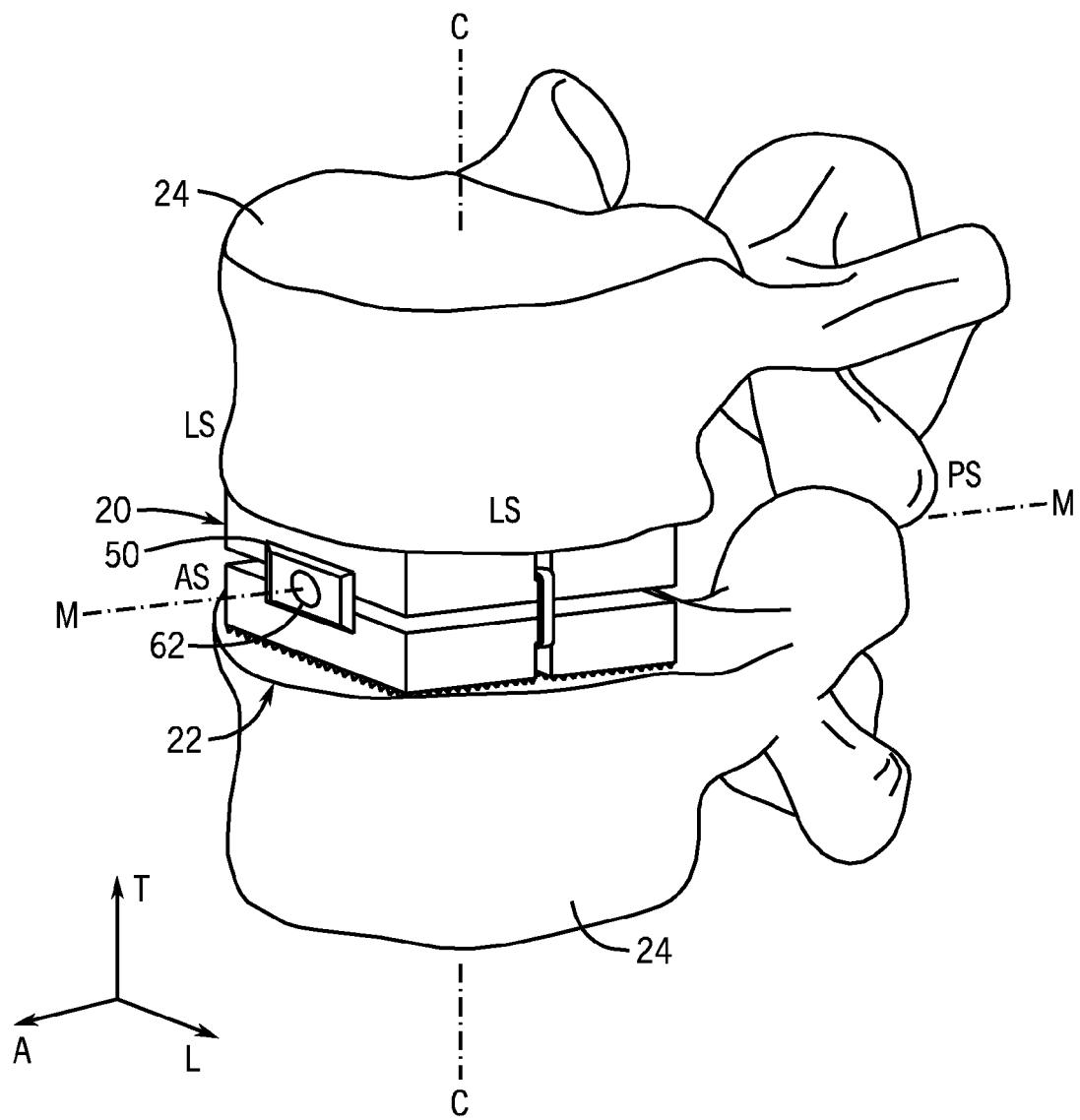
FIG. 1A is a perspective view of an expandable intervertebral implant constructed in accordance with one embodiment installed in an intervertebral space.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the expandable implant, instruments and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Referring to FIG. 1A, an expandable intervertebral implant 20 is shown installed into an intervertebral disc space 22 defined by a pair of adjacent, or neighboring, upper and lower vertebrae 24. The expandable intervertebral implant 20 can be configured to fuse with the vertebrae 24. The vertebrae 24 can be lumbar vertebrae that define an anterior side AS, an opposing posterior side PS. The vertebrae 24 further define opposing lateral sides LS that are disposed on opposing sides of a central medial axis M-M that extends along a mediolateral direction. The vertebrae 24 are illustrated as being spaced along a caudocranial axis C-C. The expandable intervertebral implant 20 extends generally along a longitudinal direction L, a lateral direction A, and a transverse direction T.

Various structure is therefore described as extending horizontally along a longitudinal direction "L" and lateral direction "A", and vertically along a transverse direction "T". The housing is elongate in the longitudinal direction L. Unless otherwise specified herein, the terms "lateral," "longitudinal," and "transverse" are used to describe the orthogonal directional components of various components. The directional terms "inboard" and "inner," "outboard" and "outer," and derivatives thereof are used herein with respect to a given apparatus to refer to directions along the directional component toward and away from the geometric center of the apparatus.

It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the expandable intervertebral implant 20 and its components as illustrated merely for the purposes of clarity and illustration.

In the illustrated embodiment, the longitudinal direction L extends in an anteroposterior direction, the lateral direction A extends in the mediolateral direction, and the transverse direction T extends in the caudocranial direction. It should be appreciated, however, that the directions defined by the expandable intervertebral implant 20 could alternatively be oriented at any desirable angle between 0° and 180° with respect to the various directions defined by the vertebrae 24. For instance, the longitudinal and lateral directions of the implant could be oriented at any desirable angle between 0° and 180° with respect to the mediolateral and anteroposterior directions. As will become appreciated from the description below, the expandable intervertebral implant 20 can be inserted into the disc space 22 in an anterior direction, a posterior direction, or any alternative direction between 0° and 180° with respect to the anterior and posterior sides.

Figure 1B:
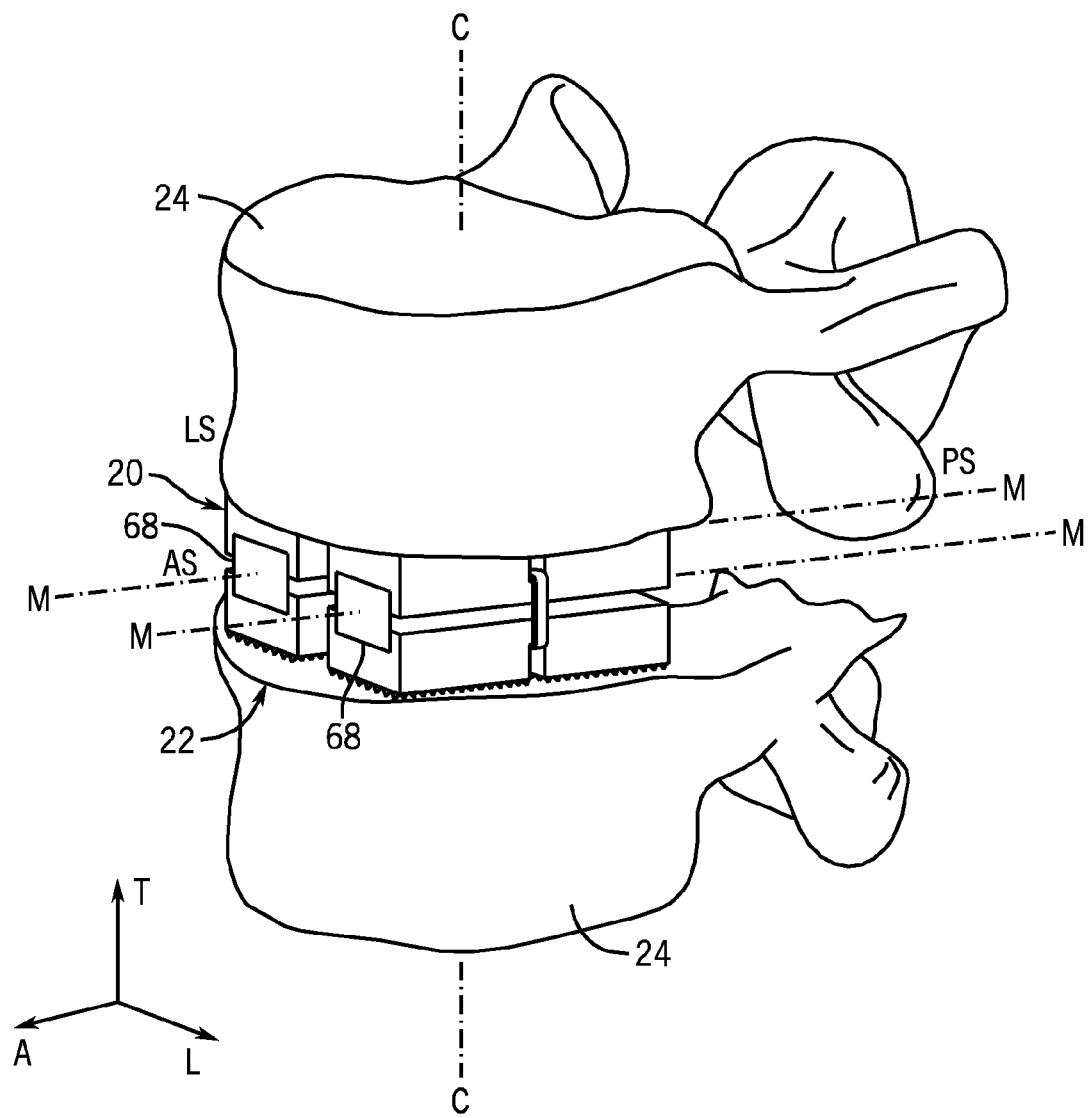
FIG. 1B is a perspective view similar to FIG. 1A, but with the intervertebral implant installed in the intervertebral space in accordance with an alternative embodiment

For instance, FIG. 1B illustrates the expandable intervertebral implant 20 installed into the intervertebral space 22 in an orientation that is 180° rotated with respect to the orientation illustrated in FIG. 1A. In this regard, it should be appreciated that the implant 20 can be inserted into the intervertebral space 22 from the anterior or posterior direction, or a direction that is angularly offset from the anterior or posterior direction. When inserting the implant 20 into the intervertebral space 22, for instance from the posterior, posterior anatomical elements can be removed, such as ligaments, a part or all of the lamina, the posterior arch, and some or all of the facet joints that are aligned with the vertebral space that receives the implant. While one implant 20 is illustrated as being inserted into the intervertebral space 22 in FIG. 1A, and a pair of implants 20 as being inserted into the intervertebral space 22 in FIG. 1B, any desired number of implants 20 can be inserted into a given intervertebral space as desired, such as between one and four implants. It should further be appreciated that one or more implants 20 can be installed into the intervertebral space 22 when performing a corpectomy or hemicorpectomy.

Figures 2A, 2B:
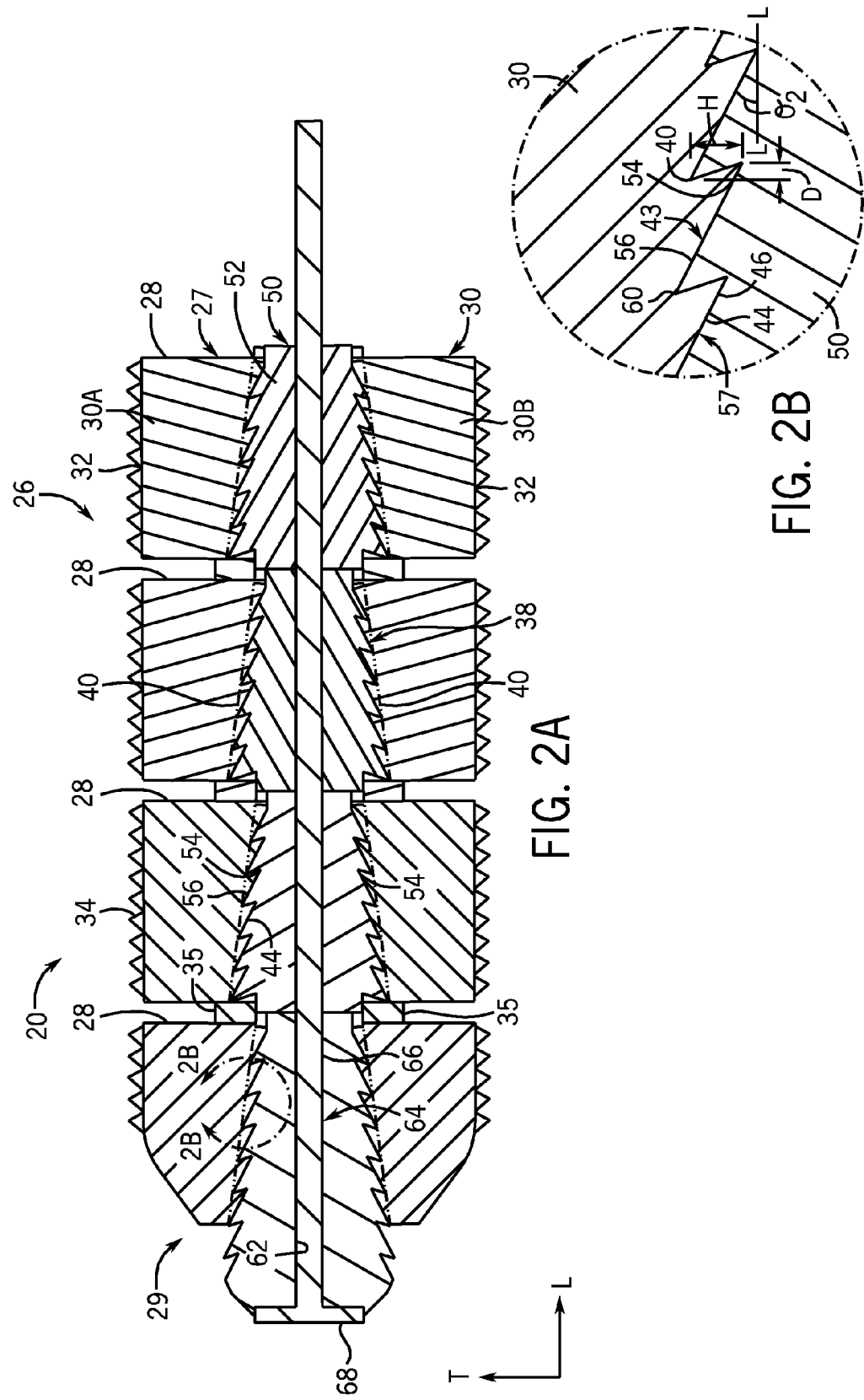
FIG. 2A is a sectional side elevation view of the expandable intervertebral implant illustrated in FIG. 1 constructed as a linkage that includes a plurality of expandable intervertebral links in accordance with one embodiment, wherein the implant is in a first contracted position.
FIG. 2B is an enlarged portion of the expandable intervertebral implant illustrated in FIG. 2A.
Figure 3A:
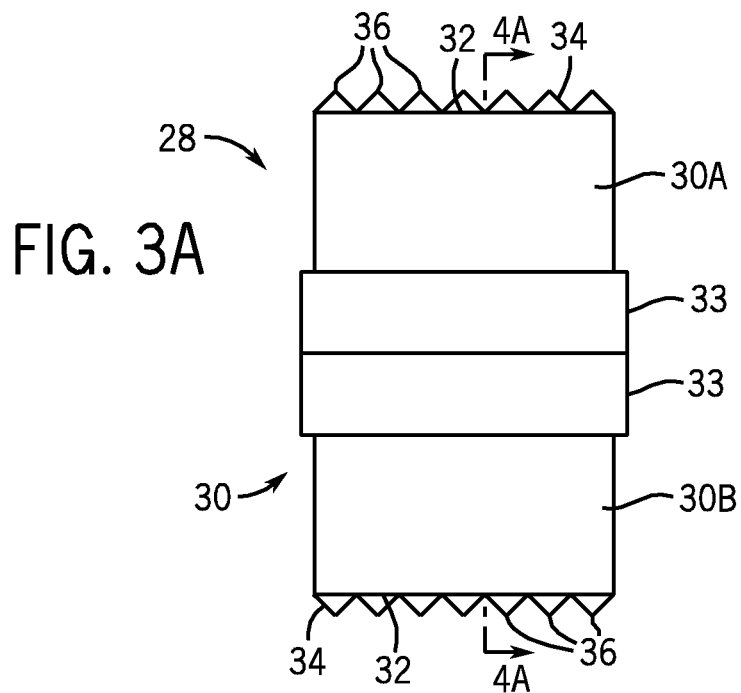
FIG. 3A is a side elevation view of an expandable intervertebral link of the intervertebral implant illustrated in FIG. 2A.
Figure 4A:
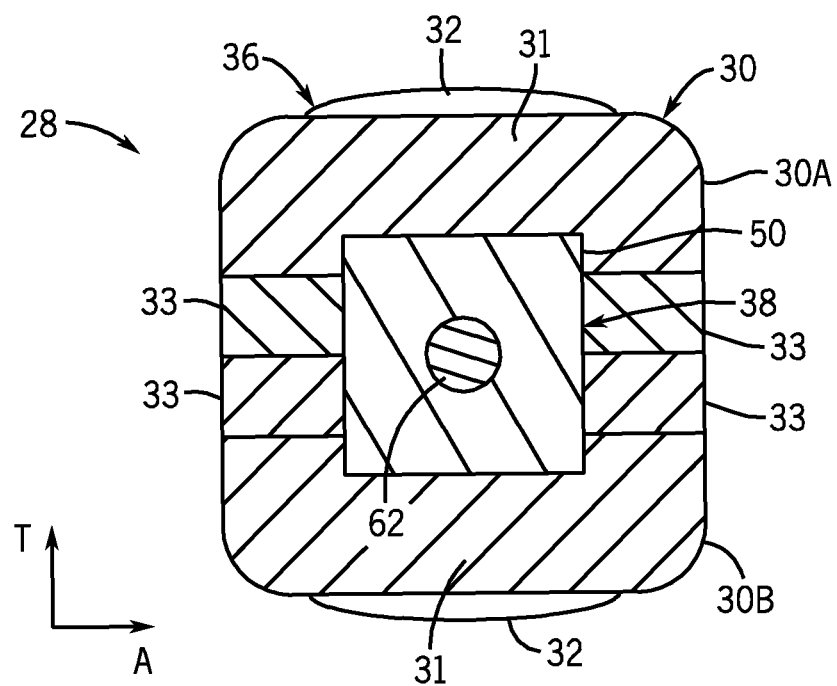
FIG. 4A is a sectional end elevation view of the expandable intervertebral link illustrated in FIG. 3A.

Referring now to FIGS. 2A, 3A, and 4A, the expandable intervertebral implant 20 can be provided as a longitudinally elongate linkage 26 that includes one or more links 28. The implant 20 can be made from any suitable biocompatible radiolucent or metallic material, such as titanium. The links 28 of the linkage 26 can be substantially similarly or identically constructed unless otherwise indicated. Each link includes an outer sleeve 30 formed from a pair of vertically opposing upper and lower outer sleeve portions 30A and 30B. The outer sleeve portions 30A and 30B each define a laterally elongate cross-beam 31 connected to a pair of outer legs 33 that each project transversely inward from the opposing outer lateral ends of the cross beams 31. Thus, the upper sleeve portion 30A includes legs 33 that project down from the laterally outer ends of the corresponding cross-beam 31, and the lower sleeve portion 30B includes legs 33 that project up from the laterally outer ends of the corresponding cross-beam 31. When the link 28 is in a first or initial contracted position, the inner transverse ends of the laterally aligned legs 33 can abut each other as illustrated so as to minimize the height of the implant 20 prior to installation into the intervertebral space 22, or they can alternatively be spaced apart.

The cross-beams 31 can each define respective vertebral engagement surfaces 32, such that the vertebral engagement surface of the upper sleeve portion 30A is an upwardly-facing surface, and the vertebral engagement surface of the lower sleeve portion 30B is a downwardly-facing surface. Each vertebral engagement surface 32 is configured to abut the corresponding upper and lower adjacent vertebrae 24.

Figure 3B:
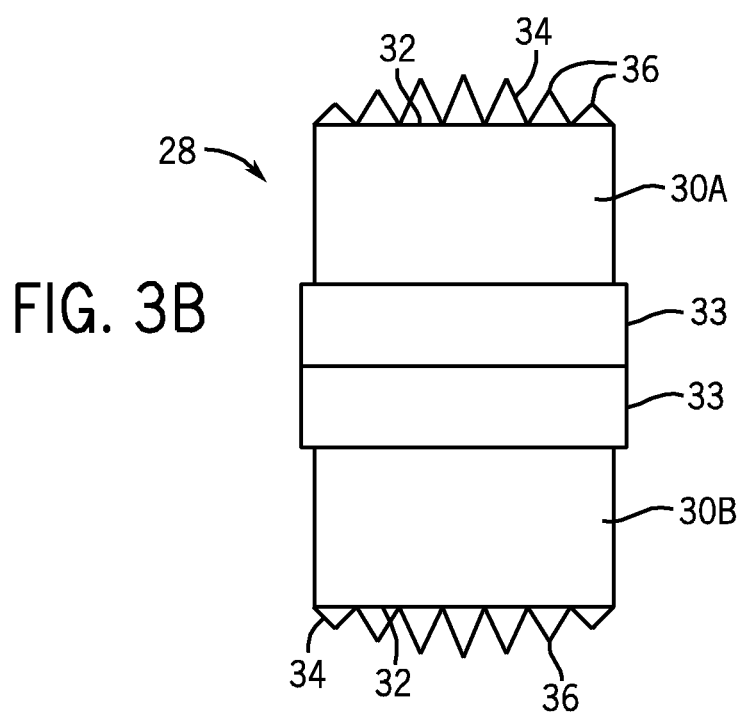
FIG. 3B is a side elevation view of the expandable intervertebral link similar to FIG. 3A, but constructed in accordance with an alternative embodiment.

Each outer sleeve portion 30A and 30B can include a plurality of teeth 34 projecting transversely out from the respective vertebral engagement surfaces 32. The teeth 34 can be laterally elongate, and can be arranged as a plurality of longitudinally spaced rows 36 as illustrated. The teeth 34 can have a substantially constant height across the plurality of rows 36, thereby defining a substantially linear toothed profile as illustrated in FIG. 3A. Alternatively, the teeth 34 can define a nonlinear profile across the rows. For instance, as illustrated in FIG. 3B, the rows of teeth of one or more links 28 can define a bowed profile, or a convexity, whereby the teeth 34 of the longitudinally middle rows have a height greater than the teeth of the longitudinally outer rows. The profile can be symmetrical or asymmetrical about a lateral axis passing through the longitudinal midpoint of the link 28.

Figure 4B:
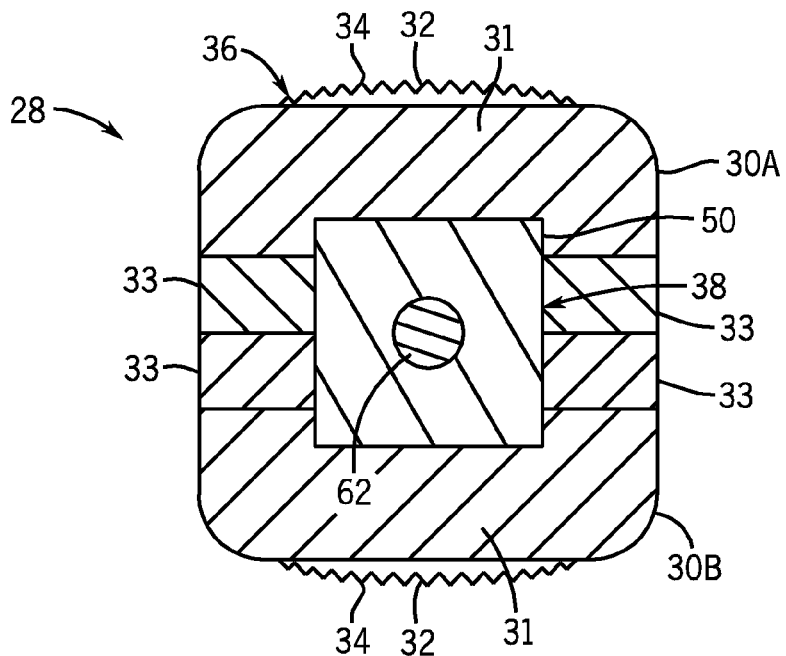
FIG. 4B is a sectional end elevation view of an expandable intervertebral link similar to that illustrated in FIG. 4A, but constructed in accordance with an alternative embodiment.

Alternatively or additionally, referring to FIG. 4A, one or more of the rows 36 of teeth 34, up to all of the rows of teeth, can be bowed along the lateral direction, such that the laterally middle portions of the teeth 34 have a height that is greater than the laterally outer portions of the teeth. The profile can be symmetrical or asymmetrical about a longitudinal axis passing through the lateral midpoint of the link 28. Thus, the teeth 34 can define a profile that is convex, or bowed, along more than one direction. While the teeth 34 are shown as being laterally elongate, it should be appreciated that the teeth 34 can alternatively be discontinuous in a lateral direction across the vertebral engagement surfaces 32 in a lateral direction. For instance, referring to FIG. 4B, a second plurality of teeth 34 can project out from the vertebral engagement surfaces 32 along the lateral direction. Thus each row 36 may include one or more teeth 34 so as to form an array of laterally spaced and longitudinally spaced teeth 34 along the vertebral engagement surfaces 32. The teeth 34 can be in substantial vertical alignment along a lateral axis, or can be bowed as shown in FIG. 4B to define a convex profile along the lateral direction such that laterally central teeth 34 have a height greater than that of the laterally outer teeth of a given row 36. Alternatively or additionally, the teeth 34 can be bowed as shown in FIG. 3B to define a convex profile along the longitudinal direction.

Figure 3C:
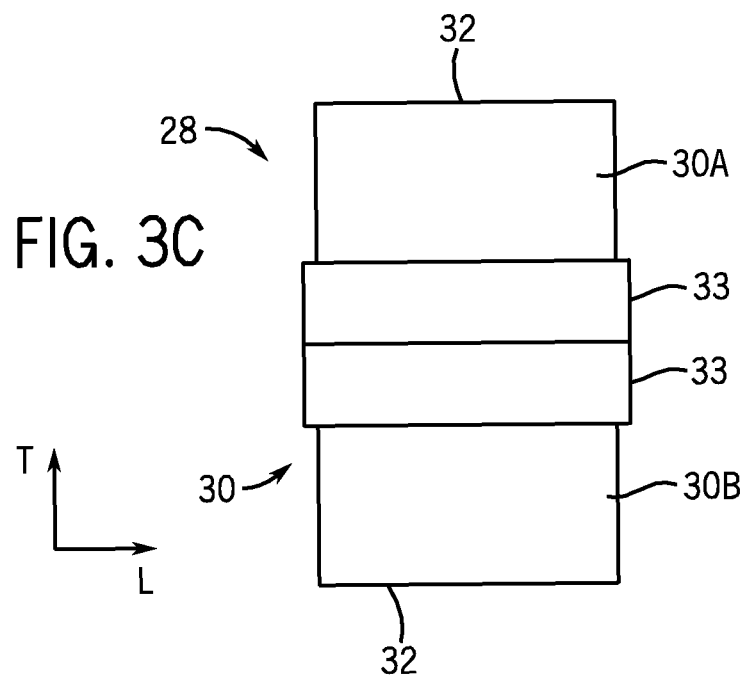
FIG. 3C is a side elevation view of the expandable intervertebral link similar to FIG. 3A, but constructed in accordance with another alternative embodiment.

The teeth 34 can assist in roughening the vertebral surface to assist in fusing the expandable intervertebral implant to the adjacent vertebrae, can provide a surface that grips against the vertebrae, and can also define an increased surface area that fuses with the adjacent vertebrae with respect to a flat vertebral engagement surface. Alternatively, one or both of the opposing vertebral engagement surfaces 32 can be substantially smooth, or non-toothed, along both the lateral and longitudinal directions, as illustrated in FIG. 3C. The smooth surface can extend substantially along a longitudinal-lateral plane, or can be bowed in either or both of the lateral and longitudinal directions.

With continuing reference to FIG. 2A, the linkage 26 can include one or more links 28, such as a plurality of adjoined links 28 as illustrated. Each link 28 can include a lateral cross beam 31 and a pair of opposing transverse legs 33 in the manner described above. Each link 28 can define a generally rectangular or square with straight or curved corners, edges, and surfaces, or any suitable alternative geometric shape. The linkage 26 defines a longitudinal front end 27 and an opposing longitudinal rear end 29. The rear end 29 of the linkage 26 can be geometrically configured for insertion into the intervertebral disc space 22. For instance, the cross beams of the link 28 disposed at the rear end 29 of the linkage can be curved transversely inward along a direction from front end 27 toward the rear end 29, thereby providing a guide surface when inserting the implant 20 into the intervertebral disc space 22.

Adjacent links 28 can be integrally connected or can alternatively be discreetly fastened to each other at a coupling location using any suitable mechanical or adhesive coupling member. For instance, a coupling member 35 can project longitudinally out from each leg 33 of adjacent links 28 toward the adjacent link 28, such that a coupling member 35 of the upper sleeve portion 30A of one link 28 is attached to a corresponding coupling member 35 of the upper sleeve portion 30A of an adjacent link 28. Likewise, a coupling member 35 of the lower sleeve portion 30B of one link 28 is attached to a corresponding coupling member 35 of the lower sleeve portion 30B of an adjacent link 28. The coupling members 35 can be flexible or rigid, and can be integrally formed with, or discreetly connected to, the corresponding legs 33. The linkage 26 can include any number of links 28 as desired, such that the upper sleeve portions 30A of each link 28 are connected, and the lower sleeve portions 30B of each link 28 are connected.

Figure 5:
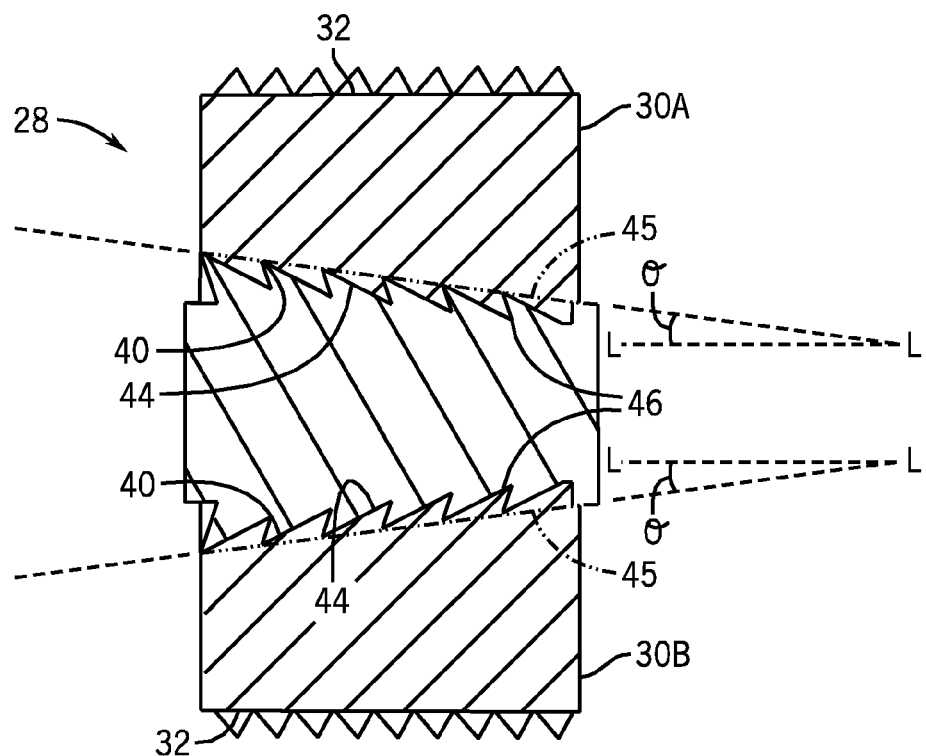
FIG. 5 is a sectional side elevation view of the expandable intervertebral link illustrated in FIG. 2A.

Referring now to FIGS. 2A and 5, the cross beam 31 of each outer sleeve portion 30A and 30B defines an outer vertebral engagement surface 32 as described above, and further defines an opposing transverse inner engagement surface 40 that extends laterally between the opposing transverse legs 33. The inner engagement surface 40 is sloped vertically so as to define an angle θ with respect to a longitudinal axis L-L that can be between 0° and 90°, for instance between about 10° and about 50°, such that the engagement surface 40 of each outer sleeve portion slopes transversely in along a longitudinal direction from the rear end 29 toward the front end 27 of the linkage 26. Thus, the inner engagement surface 40 of the upper sleeve portion 30A slopes vertically down along a longitudinal direction from the rear end 29 toward the front end 27, and the inner engagement surface 40 of the lower sleeve portion 30B slopes vertically up along a longitudinal direction from the rear end 29 toward the front end 27.

The engagement surfaces 40 of the upper sleeve portions 30A can define an angle greater θ or less than that of the engagement surfaces 40 of the lower sleeve portions 30B, thereby causing the upper sleeve portion 30A to expand at a higher or lower expansion rate, respectively, relative to the lower sleeve portion 30B. In this regard, it should be appreciated that the angle θ of one of the inner engagement surfaces 40 relative to the longitudinal axis L-L could be zero, while the angle θ of the other engagement surface 40 relative to the longitudinal axis L-L is non-zero, thereby causing only the outer sleeve portion of the other engagement surface to expand during operation.

The inner engagement surfaces 40 of each link 28 can be aligned with, and extend parallel to, the engagement surfaces 40 of the other links 28 of the linkage 26. Thus, the outer sleeve 30 of each link 28 can extend transversely a distance at its front end greater than at its rear end. Each link 28 can further include an engagement member as one or more projections or that extends transversely in from the engagement surfaces 40. The projections can be in the form of ridges, teeth, or like structure that is configured to mate with a complementary structure to fixes the implant in an expanded position. In the illustrated embodiment, the projections are shown as reverse angled teeth 44 that project transversely in from the engagement surface 40. Thus, for the purposes of description, the engagement member, or one or more projections, is referred to herein as teeth.

The teeth 44 project down from the engagement surface 40 of the upper sleeve portion 30A, and teeth project up from the engagement surface 40 of the lower sleeve portion 30B. The teeth 44 can define a root end 45 that is substantially in-line with the corresponding engagement surfaces 40, and triangular tips 46 that are transversely offset from the engagement surface. Adjacent tips 46 can be spaced apart any desired distance, such as between about 0.5 mm and about 5 mm. The teeth 44 of each link 28 can be substantially identically sized and shaped, such that a line connecting the tips 46 of adjacent teeth 40 extends parallel to the engagement surface 40. The outer sleeve portions 30A and 30B further define pockets 43 disposed between and defined by adjacent teeth 44. The pockets 43 thus have a size and shape substantially identical to the adjacent teeth 44 that define the pockets 43.

Each link 28 defines an internal void 38 that extends transversely between opposing cross beams 31 and laterally between opposing legs 33 of each outer sleeve portion 30A and 30B. The linkage 26 includes an inner core 50 that is disposed within the internal void 38 of each link 28, and is retained by the outer sleeve portions 30A and 30B. The inner core 50 can abut the transverse inner surfaces 40 of the cross beams 31 such that, during operation, longitudinal movement of the inner core 50 relative to the outer sleeve 30 causes the outer sleeve 30 to expand in a first direction, such as the vertical direction (see FIG. 7) and alternatively or additionally a second direction perpendicular to the transverse or vertical direction, such as the horizontal direction (see FIGS. 15A-C).

In the embodiment illustrated in FIGS. 2A-2B, the inner core 50 includes a core body 52 that defines opposing lateral surfaces that can face or abut the legs 33 of the outer sleeve, and opposing transverse outer, or upper and lower, engagement surfaces 54. The portion of the inner core 50 disposed within one of the links 28 can be integrally connected or alternatively fastened to the portions of the inner core 50 that are disposed in the other links 28 of the linkage 26 using any suitable mechanical or adhesive fastening member.

When the inner core 50 is installed in the internal void 38 of the outer sleeve 30, the engagement surfaces 54 can mate with, or abut, the corresponding sloped engagement surfaces 40 of the outer sleeve portions 30A and 30B. The engagement surfaces 54 are thus transversely sloped with respect to the longitudinal axis L-L, and thus extend parallel to the corresponding engagement surfaces 40. The inner core 50 can further include an engagement member as one or more projections that extend transversely out from the engagement surfaces 54. The projections can be in the form of ridges, teeth, or like structure that is configured to mate with a complementary structure to fix the implant in an expanded position. In the illustrated embodiment, the projections are shown as reverse angled teeth 56 that project transversely out from the engagement surfaces 54. Thus, for the purposes of description, the engagement member, or one or more projections, is referred to herein as teeth 56.

The teeth 56 can be sized and shaped substantially identical with respect to teeth 44, so as to mate with teeth 44. The teeth 56 define a root end that is substantially in-line with the corresponding engagement surfaces 54, and triangular tips 60 that are transversely offset from the engagement surface. The teeth 56 are identically sized and shaped, such that a line connecting the tips 60 of adjacent teeth 56 extends parallel to the engagement surface 54. Thus, the teeth of the inner core 50 become transversely inwardly disposed along a direction from the rear of the link 28 toward the front of the link 28. The inner core body 52 further defines pockets 57 disposed between and defined by adjacent teeth 56. The pockets 57 thus have a size and shape substantially identical to the adjacent teeth 56 that define the pockets 57.

With continuing reference to FIG. 2B, the teeth 44 are sized and shaped to interlock with mating teeth 56, and reside in the pockets 57 defined between adjacent teeth 56. Likewise, the teeth 56 are sized and shaped to interlock with mating teeth 44, and reside in the pockets 43 defined between adjacent teeth 44. The teeth 44 and 56 can define a sawtooth shape that is undercut such that the tips 46 and 60 of interlocking teeth 44 and 56 overlap each other a distance D, which can be greater than 0 mm and less than or equal to 2 mm. Accordingly, a transverse compressive force applied to the link 28 causes the teeth 44 and 56 to cam along each other to an interlocked position, such that interference between the tip ends 46 and 60 resists vertical separation of the outer sleeve 30 from the inner core 50 during insertion of the implant 20 into the intervertebral space. Moreover, as the implant 20 is inserted into the disc space 22, the bodily tissue will apply a forward longitudinal force against the outer sleeve 30, thereby biasing the teeth 44 and 56 into their interlocked position, whereby motion of the core 50 relative to the outer sleeve 30 is permitted in the longitudinally forward direction, but prevented in a longitudinally rearward direction.

The opposing tips 46 and 60 of interlocking teeth 44 and 56 can be spaced a transverse distance so as to define a height H that can be within a range between 0 mm and about 3 mm. The teeth 44 and 56 can further define an angle $\theta_2$ between about 10° and about 50° with respect to the longitudinal axis L-L.

Figure 6:
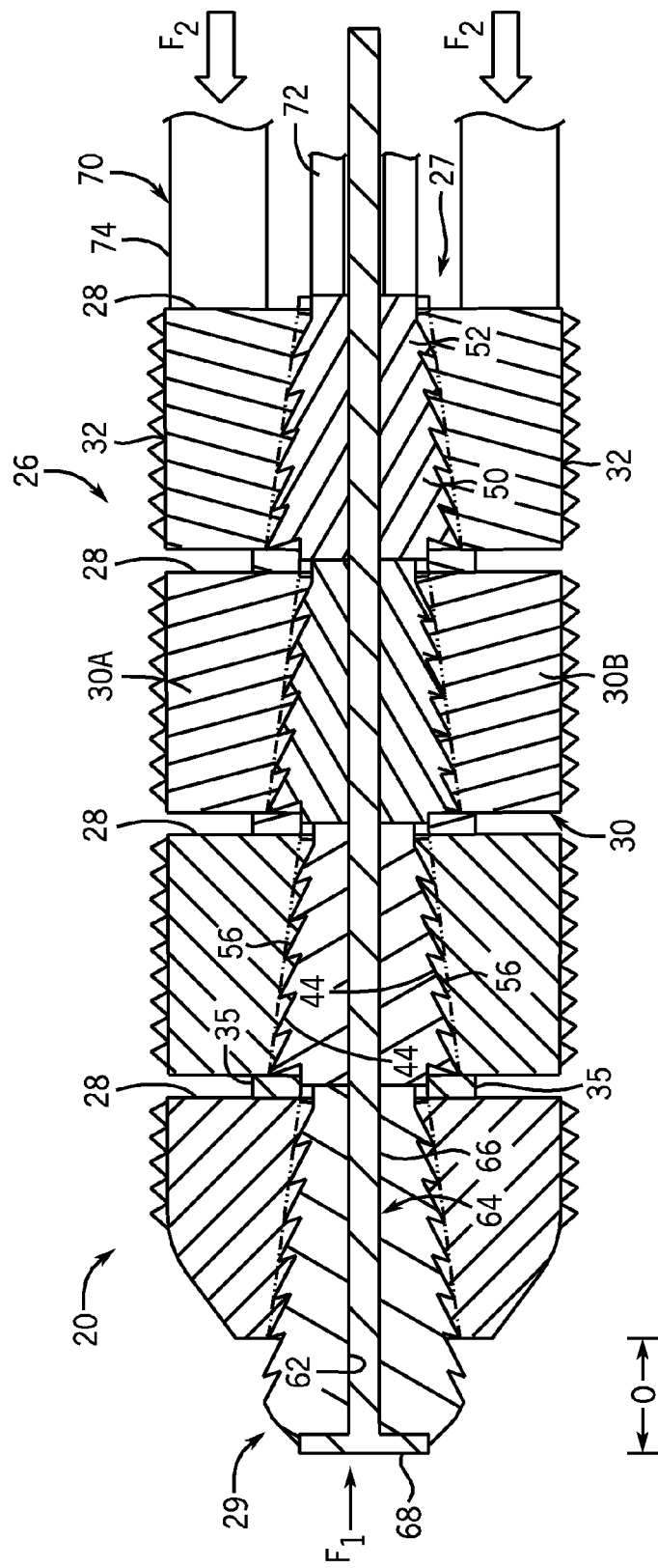
FIG. 6 is a sectional side elevation view of the expandable intervertebral implant illustrated in FIG. 5A, connected to an insertion device.

Referring now to FIG. 6, the linkage 26 can be coupled to an insertion tool 70, which includes a biasing member 64, an inner holding sleeve 72, and an outer holding sleeve 74. The biasing member 64 is operable to move the inner core member 50 longitudinally forward relative to the outer sleeve 30. In the illustrated embodiment, the inner core body 52 defines an internal longitudinally elongate bore 62 that is sized and shaped to receive the biasing member 64, which can be provided as a longitudinally extending rod or wire 66 connected to a transverse stopper 68 at one longitudinal end of the wire 66. The wire 64 can be made from vitalium, titanium, or the like. The stopper 68 is sized and shaped to abut the rear surface of the inner core 50, but not the outer sleeve, of the rearmost link 28, and the wire 66 can extend through the bore 62 of all inner core bodies 52 along the linkage 26, and project forward from the front end 27 of the linkage. The wire 66 can be held in place inside the bore 62 by an interference fit or any suitable fixation mechanism.

The inner annular holding sleeve 72 surrounds the wire 66 at a location forward from the front end 27 of the linkage 26, and can guide the wire 66 during operation. The wire 66 can be pulled in a longitudinal forward direction relative to the inner holding sleeve 72 such that the inner holding sleeve 72 abuts the front end of the core body 52 of the front-most link. The engagement of the inner holding sleeve 72 and the core body 52 allows a user to maintain control of the position of the implant 20 during insertion into the intervertebral space 22 as tension is applied to the wire 66.

The outer annular holding sleeve 74 is configured to abut the front end of the forwardmost outer sleeve 30 at a location that is out of transverse alignment with the core body 52. The outer holding sleeve 74 provides reciprocal biasing member that is operable to provide a biasing force that is equal and opposite to the force applied from the biasing member 64 to the core 50. In this regard, the outer holding sleeve 74 can be referred to as a brace member.

Accordingly, as a first force $F_1$ is applied to the wire 66 along a longitudinally forward direction, the stopper 68 applies a corresponding longitudinally forward biasing force to the rear link 28. The outer holding sleeve 74 applies a force $F_2$ into the outer linkage sleeve 30 that is equal and opposite with respect to the force $F_1$. The force $F_1$ applied to the wire 62 thus causes the inner core 50 to translate longitudinally forward with respect to the outer sleeve 30.

Figure 7:
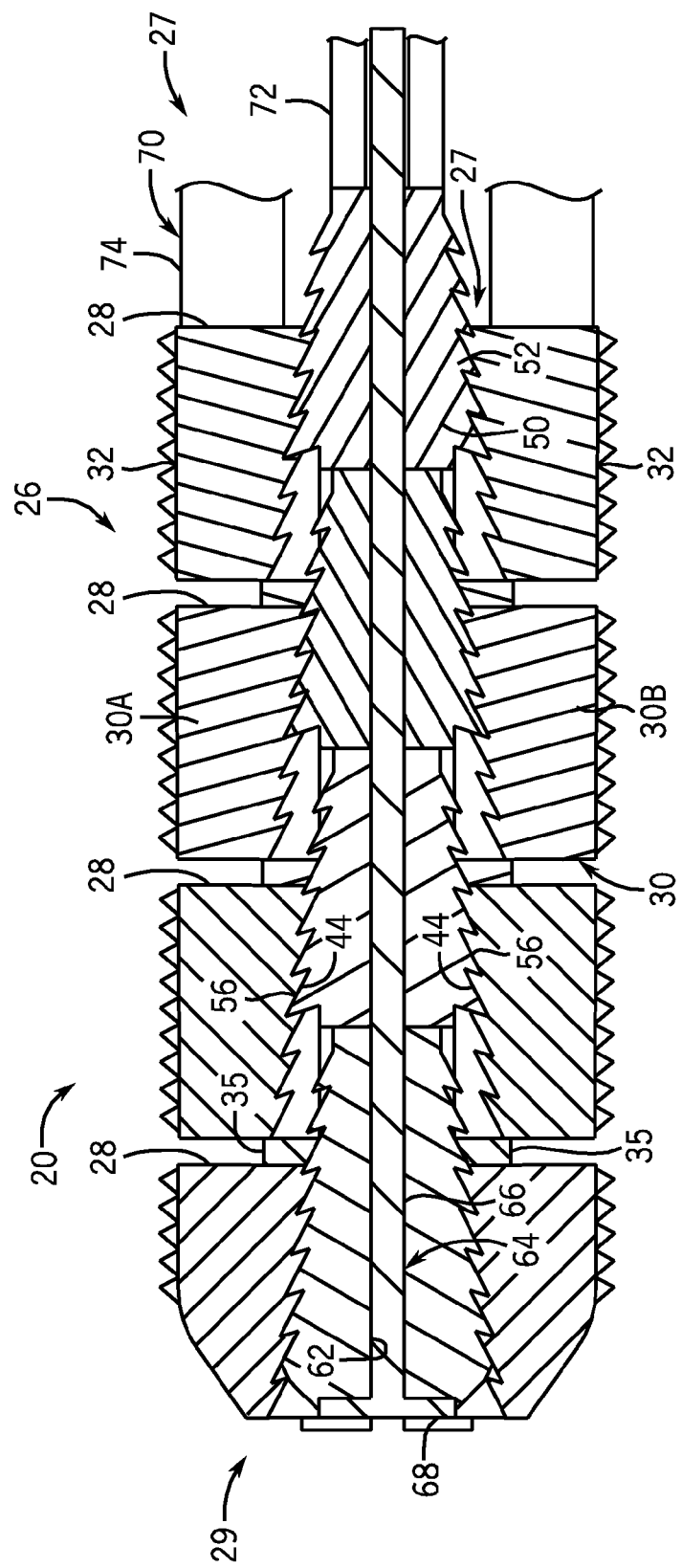
FIG. 7 is a sectional side elevation view of the expandable intervertebral implant illustrated in FIG. 6, but illustrated in a second vertically expanded position.

Referring also to FIG. 7, as the inner core 50 translates forward with respect to the outer sleeve 30, the engagement surfaces 40 ride along the complementary engagement surfaces 54, thereby causing the outer sleeve portions 30A and 30B to deflect vertically away from each other. As the outer sleeve portions 30A and 30B deflect away from each other, the intervertebral implant 20 expands in the transverse, or vertical, direction. The slope of the upper and lower mating engagement surfaces 40 and 54 determines the rate at which the upper and lower sleeves 30A and 30B expand, respectively.

As the inner core 50 moves in the forward direction with respect to the outer sleeve 30, the tips 46 and 60 of the engagement members, or teeth 44 and 56, cam over each other, thus causing the height of the implant 20 to increase in increments substantially equal to the height H of the teeth 44 and 56. Once a desired height is achieved and the biasing force is removed from the wire 62, the engaging teeth 44 and 56 can allow slight relative motion of the outer linkage sleeve 30 relative to the inner core 50 in the longitudinally forward direction, which can cause the outer teeth 34 of the sleeve to scuff the inner surfaces of the adjacent vertebrae 24, thereby facilitating fusion of the sleeve portions 30A and 30B to the vertebrae 24.

Once the teeth 44 and 56 become interlocked, relative motion between the inner core 50 and the outer sleeve 30 is prevented in the absence of the application of another biasing force to the cable 66. It should thus be appreciated that the linear forward motion of the inner core 50 relative to the outer sleeve 30 causes the intervertebral implant 20, or outer sleeve portions 30A and 30B, to expand from an initial, or relaxed position having a first height, to a second or an expanded position having a second height that is greater than the first height. The teeth 44 and 56 provide engagement members that prevent the outer sleeve portions 30A and 30B from contracting toward each other once the intervertebral implant 20, sleeve outer portions 30A and 30B, have reached the desired expanded position. It should be appreciated that while the engagement surfaces 40 and 54 of each link 28 each include a plurality of corresponding teeth, each engagement surfaces 40 and 54 could alternatively comprise one or more teeth.

During operation, the implant 20 is inserted into the intervertebral space 22 in the initial position, and subsequently expanded to a second expanded position so as to abut and position the adjacent vertebrae 24 to a desired vertical position that causes the intervertebral space to achieve a desired height. The intervertebral implant 20 can thus be referred to as an intervertebral spacer that causes the intervertebral space 22 between adjacent vertebrae to increase to a desired caudocranial height. An autograft or bone substitute can be placed around the implant 20 in the intervertebral space 22 if desired.

It should be appreciated that, as shown in FIG. 6, the core body 52 of the rear link 28 can be sized having a longitudinal length that is substantially longer than that of the corresponding outer sleeve 30. As a result, the core 50 can project rearward with respect to the sleeve 30 of the rearmost link 28 by an offset distance "O" when the implant 20 is in the initial or relaxed position. The offset distance O can be preselected based, for instance, on the slope of the engagement surfaces 44 and 54 and the desired expansion of the outer sleeve 30, such that once the implant 20 has reached the desired final height, the rear surface of the core 50 can be substantially flush with the rear surface of the outer sleeve 30 the rear link 28, as shown in FIG. 7.

Moreover, FIG. 6 shows the front end of the core body 52 of the front linkage 28 as being substantially flush with the front end of the outer sleeve 30 of the front linkage 28 when the implant 20 is in the initial position. Accordingly, as shown in FIG. 7, when the implant is in the expanded position, the front end of the core body 52 of the front linkage 28 extends forward from the front end of the outer sleeve 30 of the front linkage 28. It should be appreciated, however, that the front end of the core body 52 of the front linkage 28 could alternatively be recessed with respect to the front end of the outer sleeve 30 of the front linkage 28 a distance equal to the offset distance O when the implant 20 is in the initial position. Accordingly, when the implant 20 is in the expanded position, the front end of the core body 52 of the front linkage 28 could be substantially flush with the front end of the outer sleeve 30 of the front linkage 28.

Figure 8A:
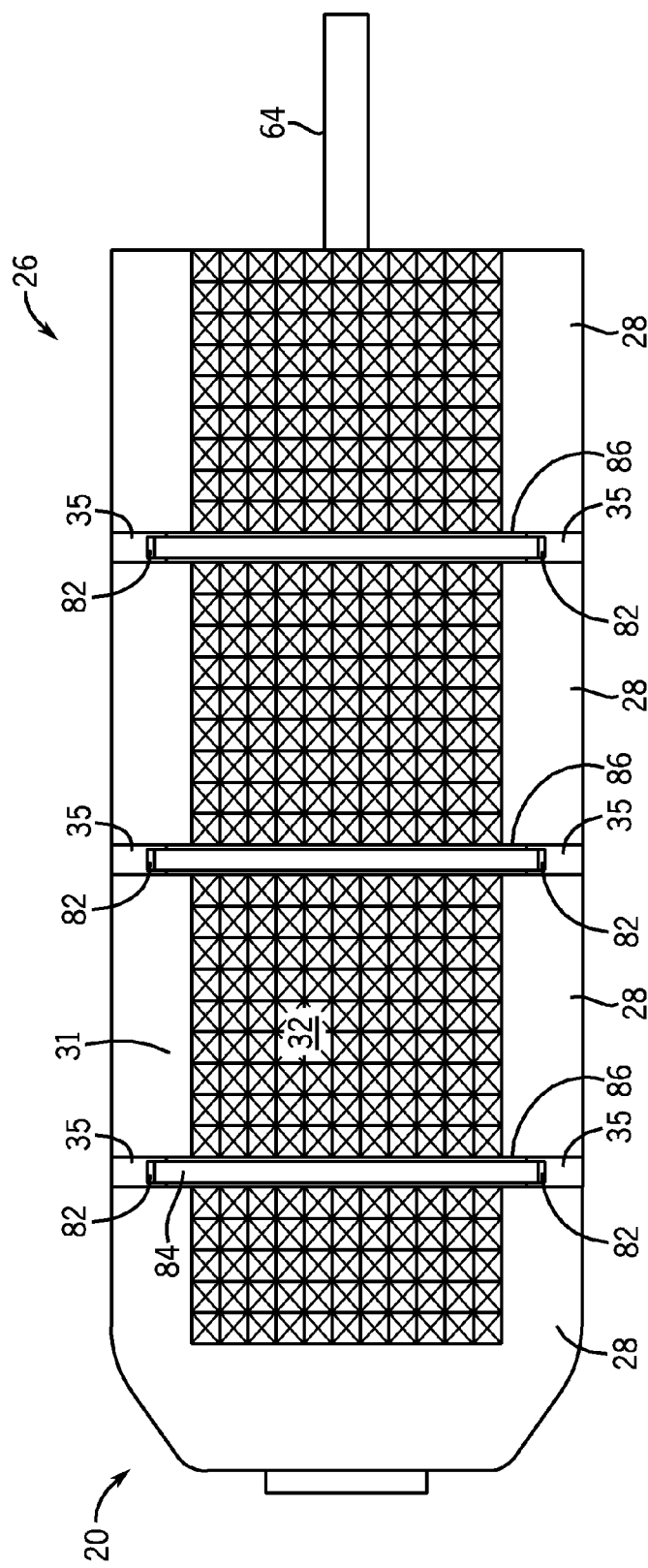
FIG. 8A is a top plan view of the expandable intervertebral implant illustrated in FIG. 7, including a retainer that secures various components of the expandable intervertebral implant.
Figure 8B:
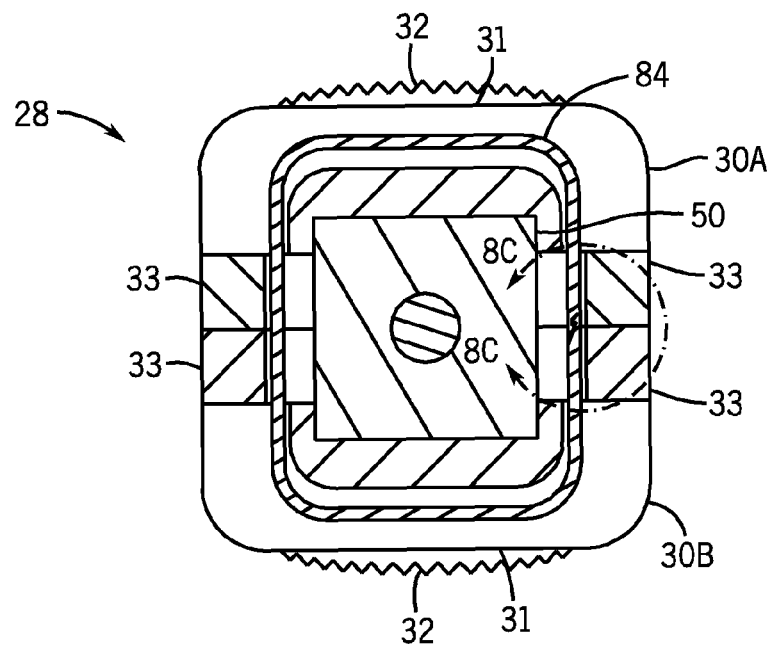
FIG. 8B is a sectional end view of the expandable intervertebral implant as illustrated in FIG. 8A.
Figure 8C:
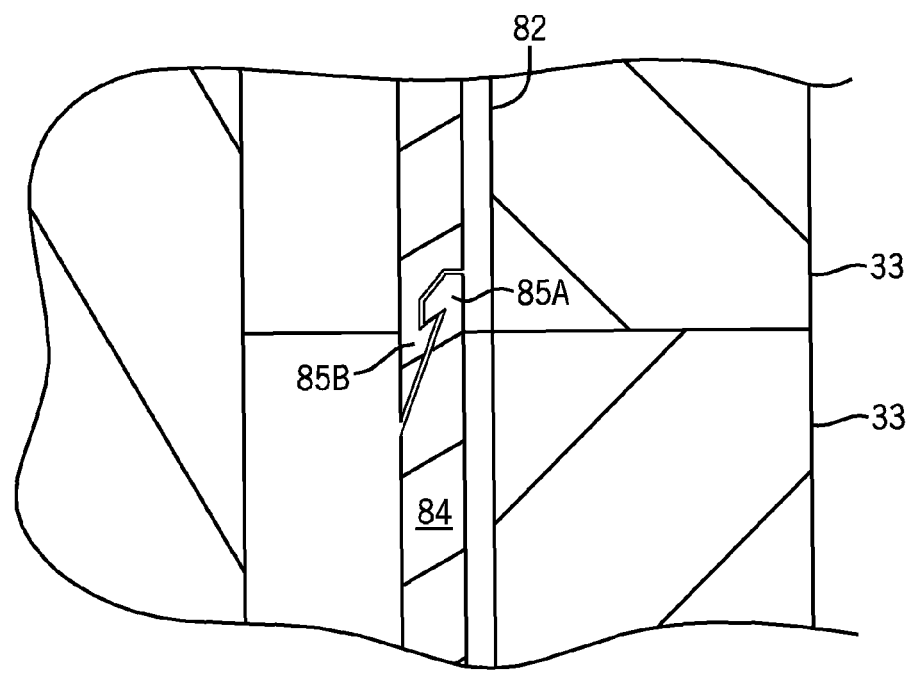
FIG. 8C is an enlarged view of a portion of the expandable intervertebral implant illustrated in FIG. 8B.

Referring now to FIGS. 8A-C, the expandable intervertebral implant 20 can include a retainer member in the form of one or more, such as a plurality of, bands 84 that are configured to apply a compressive retention force against the links 28 that can assist in maintaining the structural integrity of the implant 20 as the implant 20 is inserted into the intervertebral space 22 and expanded to the vertically expanded position. In particular, the linkage 26 can include laterally opposing transverse slots 82 that extend vertically through the coupling members 35. The coupling members 35 can include a lateral portion that extends in a laterally extending groove 86 disposed between adjacent links 28.

A metallic or elasticized band 84 can be inserted through the laterally opposing slots 82 and sit in the grooves 86 such that the band 84 surrounds the legs 33 of the outer sleeve portions 30A and 30B. The band 84 can include terminal ends 85A and 85B that form an interlocking tongue-and-groove. Thus, the terminal ends 85A and 85B can be clipped together, and the terminal ends can be placed inside one of the slots 82 so as to reduce the possibility that the band 84 would be inadvertently separated. The bands 84 can apply a compressive force that biases the outer sleeve portions 30A and 30B against each other and against the inner core 50, thereby assisting in the retention of the teeth 44 and 56 in their interlocked configuration. The bands 84 can be radiolucent so as to provide an indication of the position and angular orientation of the implant 20 during the implantation procedure.

Figure 9A:
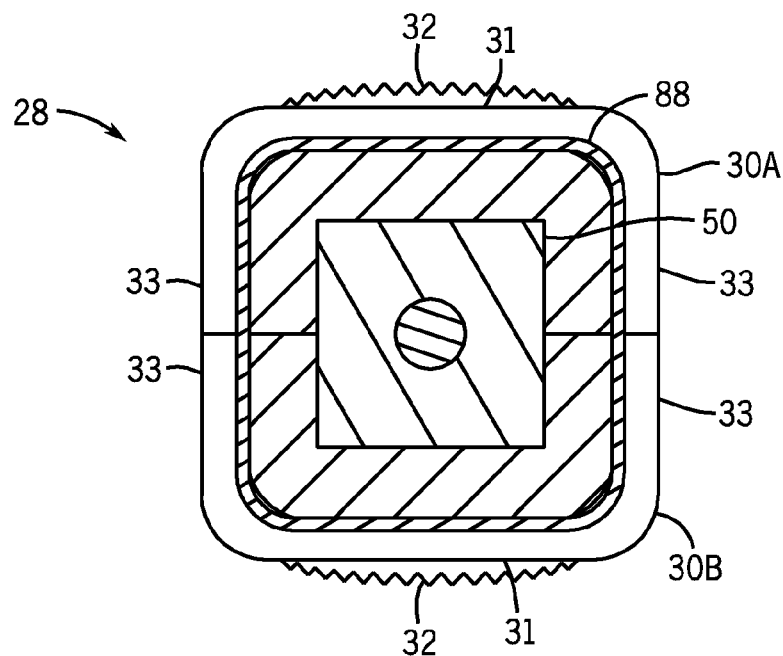
FIG. 9A is a sectional end view of the expandable intervertebral implant similar to FIG. 8B, but showing a retainer constructed in accordance with an alternative embodiment.
Figure 9B:
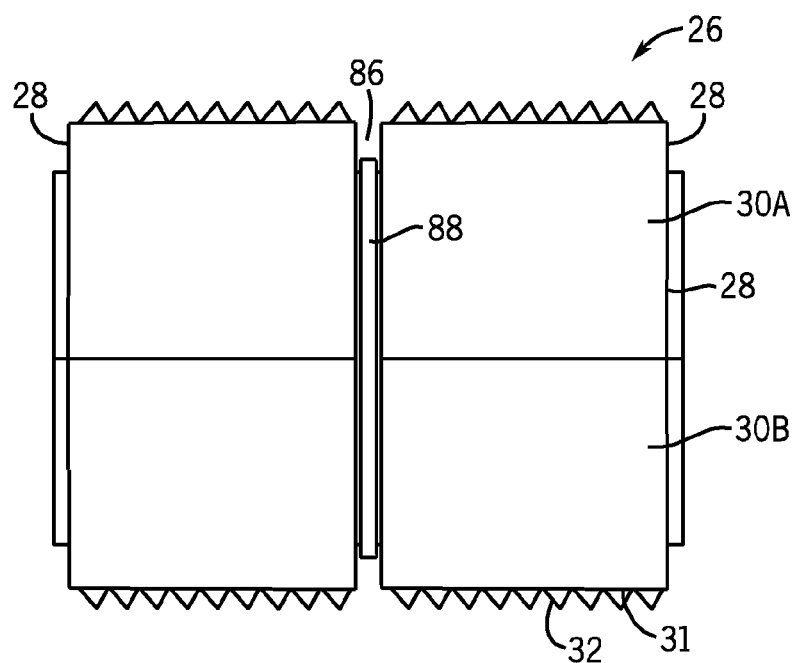
FIG. 9B is a side elevation view of the expandable intervertebral implant illustrated in FIG. 9A.

Referring now to FIG. 9A-B, the expandable intervertebral implant 20 can include a retainer member constructed in accordance with an alternative embodiment. In particular, the legs 33 do not define a transverse slot extending vertically therethrough. Instead, an elasticized band 88 can be stretched over one or more of the links 82 and inserted into the groove 86. The elasticity of the band 88 can apply a compressive force that biases the outer sleeve portions 30A and 30B against each other and against the inner core 50, thereby assisting in the retention of the teeth 44 and 56 in their interlocked configuration. The plurality of bands 88 can be radiolucent so as to provide an indication of the position and angular orientation of the implant 20 during the implantation procedure.

Figure 10:
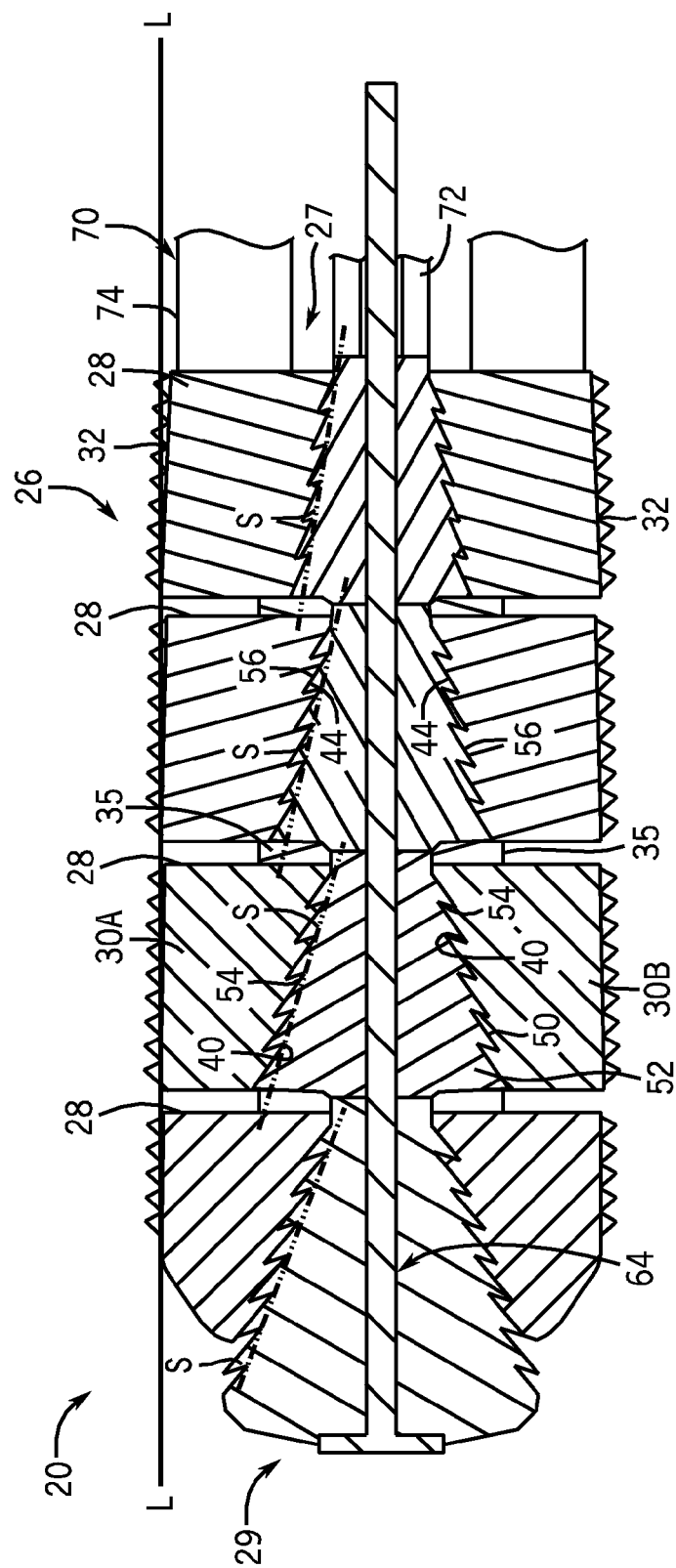
FIG. 10 is a sectional side elevation view of an expandable intervertebral implant similar to FIG. 6, but configured to provide a lordotic outer profile when expanded, in accordance with an alternative embodiment.

Referring now to FIG. 10, the expandable intervertebral implant can be constructed such that the vertebral engagement surfaces 32 define a lordotic profile when the implant 20 is in the expanded position. In accordance with the illustrated embodiment, the slope S of the engagement surfaces 40 and 54 relative to the longitudinal axis L-L of each link 28 vary from link to link. Thus, the opposing engagement surfaces 40 and 54 of one link are angled, or not parallel, with respect to the corresponding opposing engagement surfaces 40 and 54 of an adjacent link. For instance, the slope of each interfacing engagement surfaces 40 and 50 of each link 28 relative to the longitudinal axis L-L has a magnitude that decreases along a direction from the rear link 28 toward the front link 28. Thus, the magnitude of the slope of the complementary engagement surfaces 40 and 54 of a given link 28 is greater than that of forwardly disposed links 28, and less than that of rearwardly disposed links 28.

Accordingly, as the implant 20 expands, the outer sleeve portions 30A and 30B of each link 28 will become vertically displaced at different rates. In the illustrated embodiment, the rate of outer sleeve vertical displacement will decrease in a direction from the rear link 28 toward the front link 28. It should, of course, be appreciated that the slope of the engagement surfaces 40 and 50 of each link could alternatively decrease in a direction from the front link 28 toward the rear link 28 such that the rate of vertical displacement would decrease in a direction from the front link 28 toward the rear link 28. Alternatively still, the middle links 28 can expand at a rate that is greater than or less than the forward and rearward spaced links 28.

In the embodiment illustrated in FIG. 10, the vertebral engagement surfaces 32 of the opposing outer sleeve portions 30A and 30B can be substantially flat in the longitudinal direction. The slope of opposing vertebral engagement surfaces 32 of each link 28 can vary from link to link. Thus, the vertebral engagement surfaces 32 of one link are angled, or not parallel, with respect to the engagement surfaces 32 of an adjacent link. It can also be said that the engagement surfaces 32 of each link 28 are sloped at an angle with respect to the longitudinal direction that is different than the angle at which the engagement surfaces 32 of the other links are sloped relative to the longitudinal direction.

The opposing engagement surfaces 32 of the outer sleeve portions 30A and 30B of a given link 28 can be equal and opposite relative to the longitudinal axis L-L. As illustrated, the vertebral engagement surfaces 32 of the links 28 each define a slope having a magnitude with respect to the longitudinal axis L-L that decrease from link to link as the slope of the corresponding engagement surfaces 40 and 50 increase when the implant 20 is in the initial position. Thus, in the illustrated embodiment, the slope of each of the vertebral engagement surfaces 32 of the links 28 has a magnitude that decrease in direction from the front end 27 of the linkage 26 toward the rear end 29 of the linkage. The magnitude of the slope of the opposing vertebral engagement surface 32 of a given link 28 is greater than that of rearwardly disposed links 28, and less than that of forwardly disposed links. Alternatively, the slope of the opposing vertebral engagement surfaces 32 of each link 28 could be substantially identical from link to link.

Figure 11:
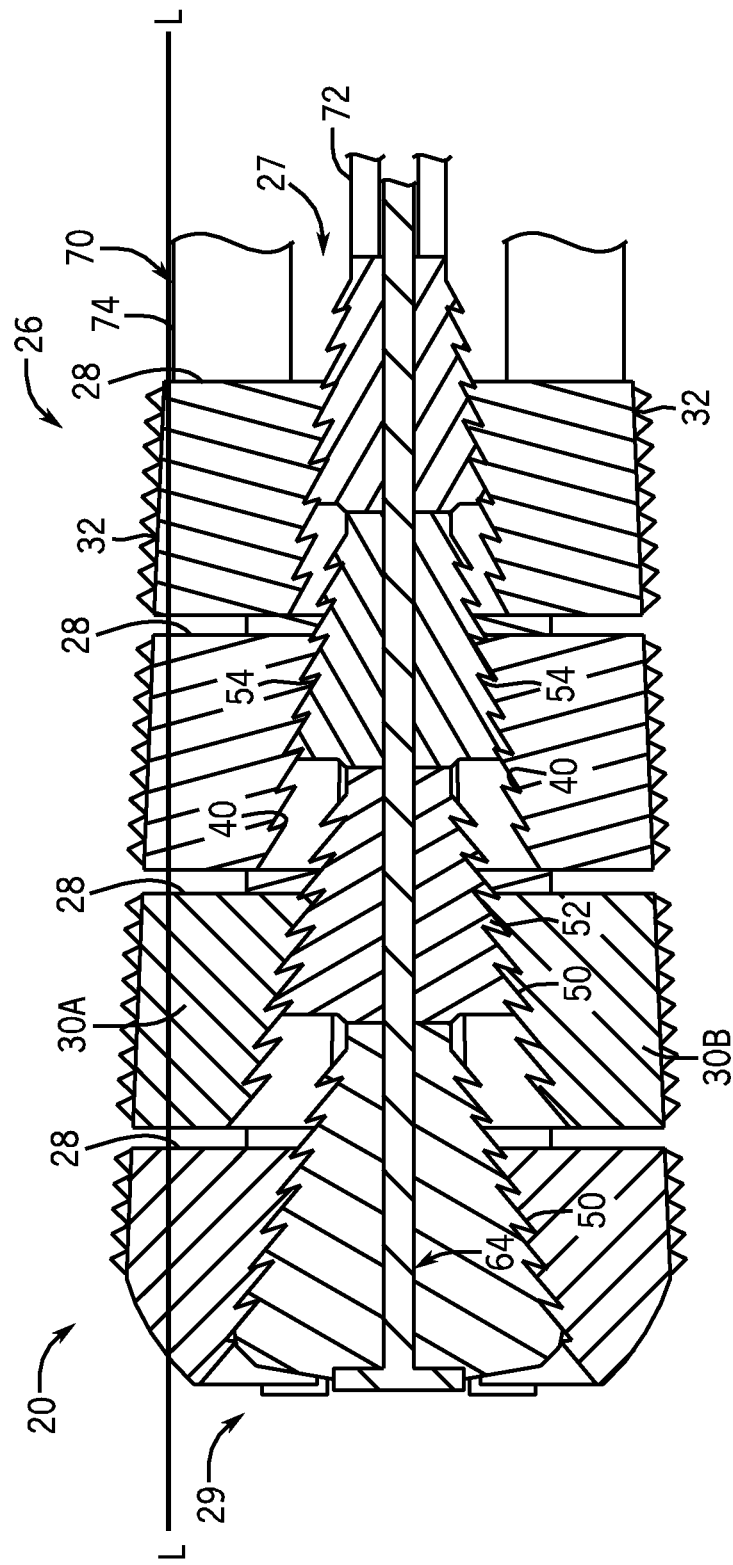
FIG. 11 is a sectional side elevation view of the expandable intervertebral implant illustrated in FIG. 10, but showing the implant in a vertically expanded position.

Referring now to FIG. 11, when the inner core 50 is moved longitudinally forward relative to the outer sleeve 30 to move the implant from the initial position to the expanded position in the manner described above, the links 28 expand at different rates. In particular, a given link 28 expands at a faster rate than forwardly disposed links, and at a rate slower than rearwardly disposed links. As a result, when the intervertebral implant 20 is in the expanded position illustrated in FIG. 11, the opposing outer sleeve portions 30A and 30B of each link 28 have expanded a distance that is greater than those of forwardly disposed links, and less than those of rearwardly disposed links. Thus, the implant 20 defines vertebral engagement surfaces 32 that are sloped transversely outward with respect to the longitudinal axis L-L in a direction from the front end 27 toward the rear end 29. Moreover, the vertebral engagement surfaces 32 of each outer sleeve portion 30A and 30B are in line with the vertebral engagement surfaces 32 of the other links 28 of the linkage 26, thereby creating reliable engagement surfaces with the vertebrae 24.

Figure 12:
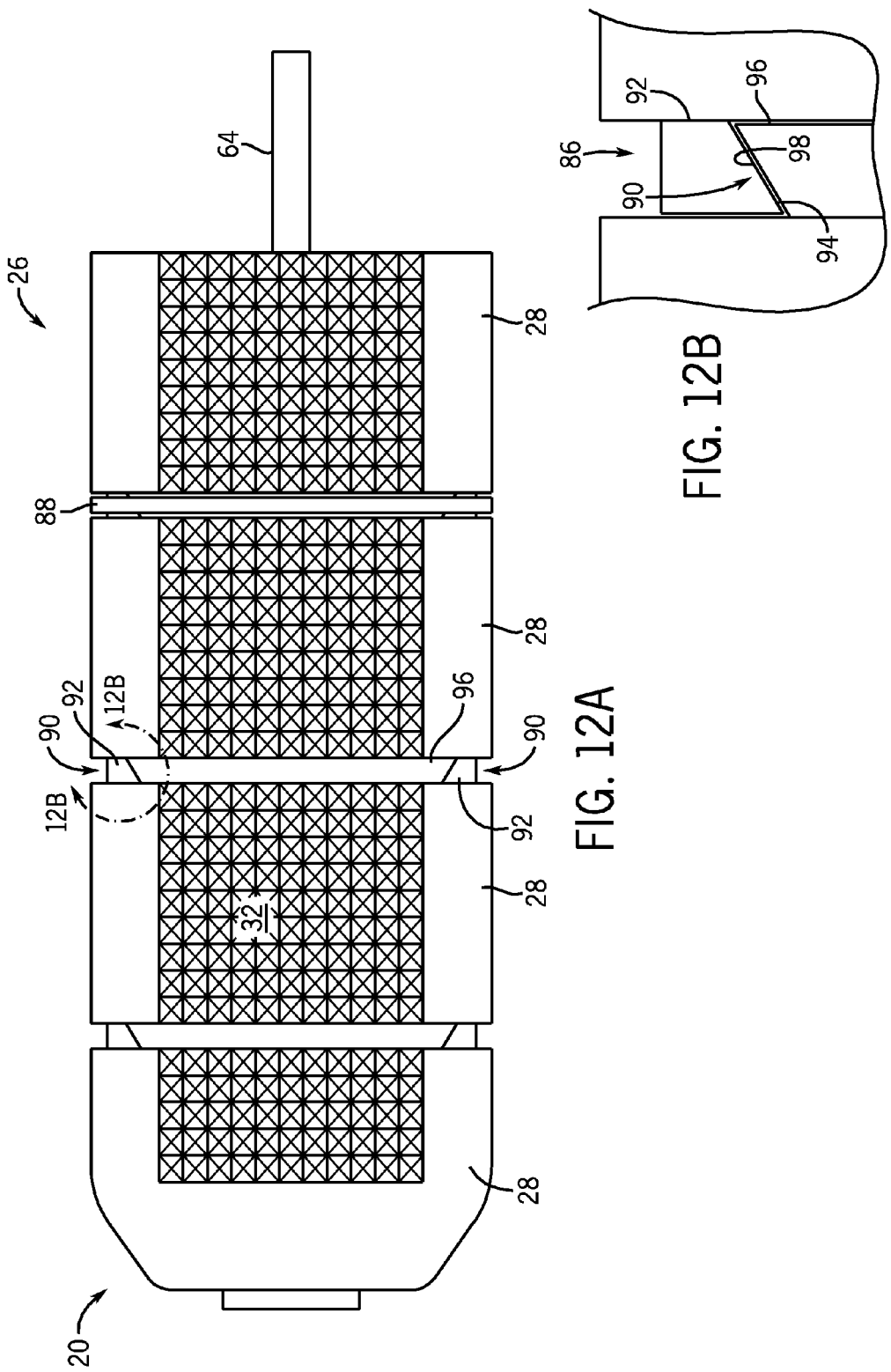
FIG. 12A is a top plan view of the expandable intervertebral implant illustrated in FIG. 10.
FIG. 12B is an enlarged side elevation view of a portion of the expandable intervertebral implant illustrated in FIG. 12A.

Referring to FIGS. 12A-B, it should be appreciated that the links 28 can be coupled so as to permit relative vertical motion between adjacent links. Accordingly, the adjacent links 28 can be coupled by a joint, such as a tongue-and-groove joint 90. The joint 90 includes a pair of first laterally opposing engagement members 92 attached to one of the adjacent links 28. The engagement members 92 extend vertically, and each includes a beveled surface 94 that slopes laterally inward along a direction longitudinally away from the link 28. The other of the adjacent links 28 includes a second laterally elongate engagement member 96 that extends laterally between the opposing engagement members 92. The engagement member extends vertically, and includes laterally opposing beveled surfaces 98 that slopes laterally outward along a direction longitudinally away from the link 28. The beveled surfaces 94 and 98 engage each other to interlock the adjacent links with respect to longitudinal separation, while allowing for relative vertical motion along the beveled surfaces 94 and 98, and thus relative vertical motion between the adjacent links 28. A retainer member, such as band 88, can further be inserted into one or more of the grooves 86 that separate the adjacent links 28 so as to further maintain the structural integrity of the linkage 26 during use in the manner described above.

Figure 13:
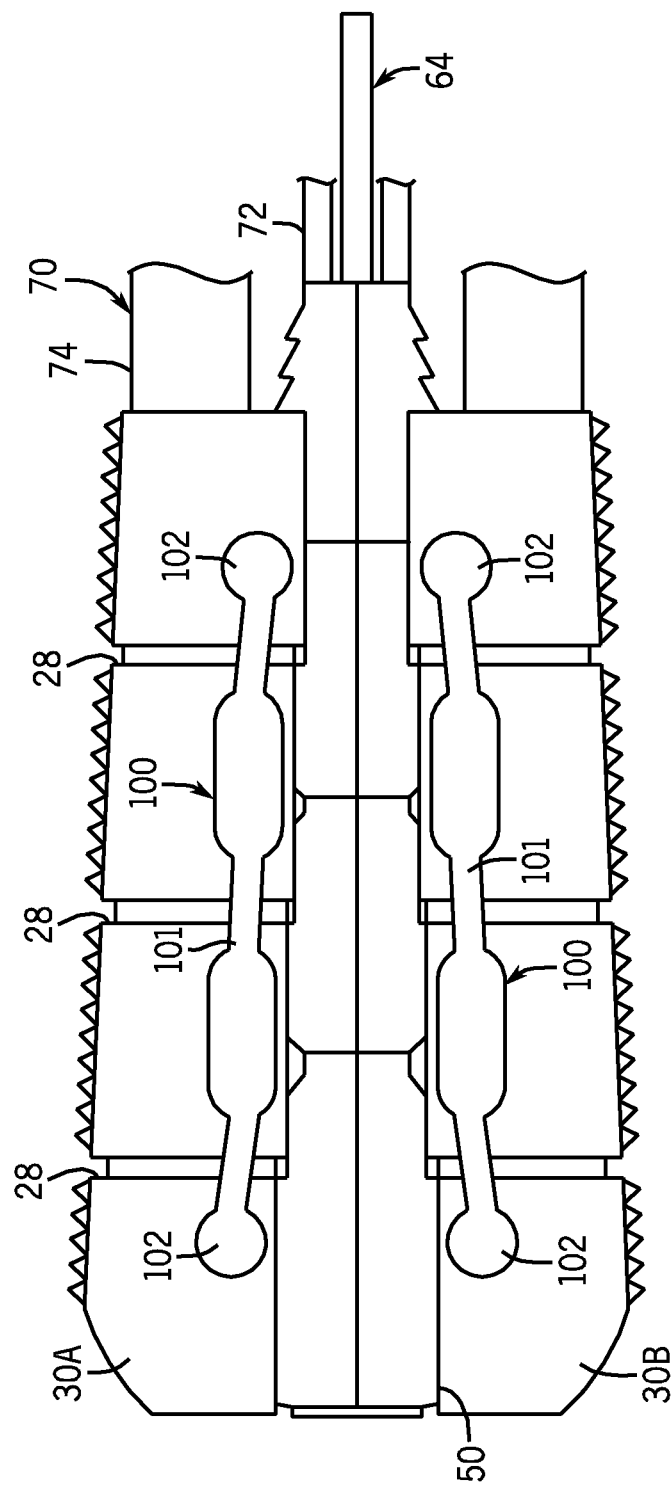
FIG. 13 is a side elevation view of an expandable intervertebral implant including a second retainer constructed in accordance with an alternative embodiment.
Figure 14:
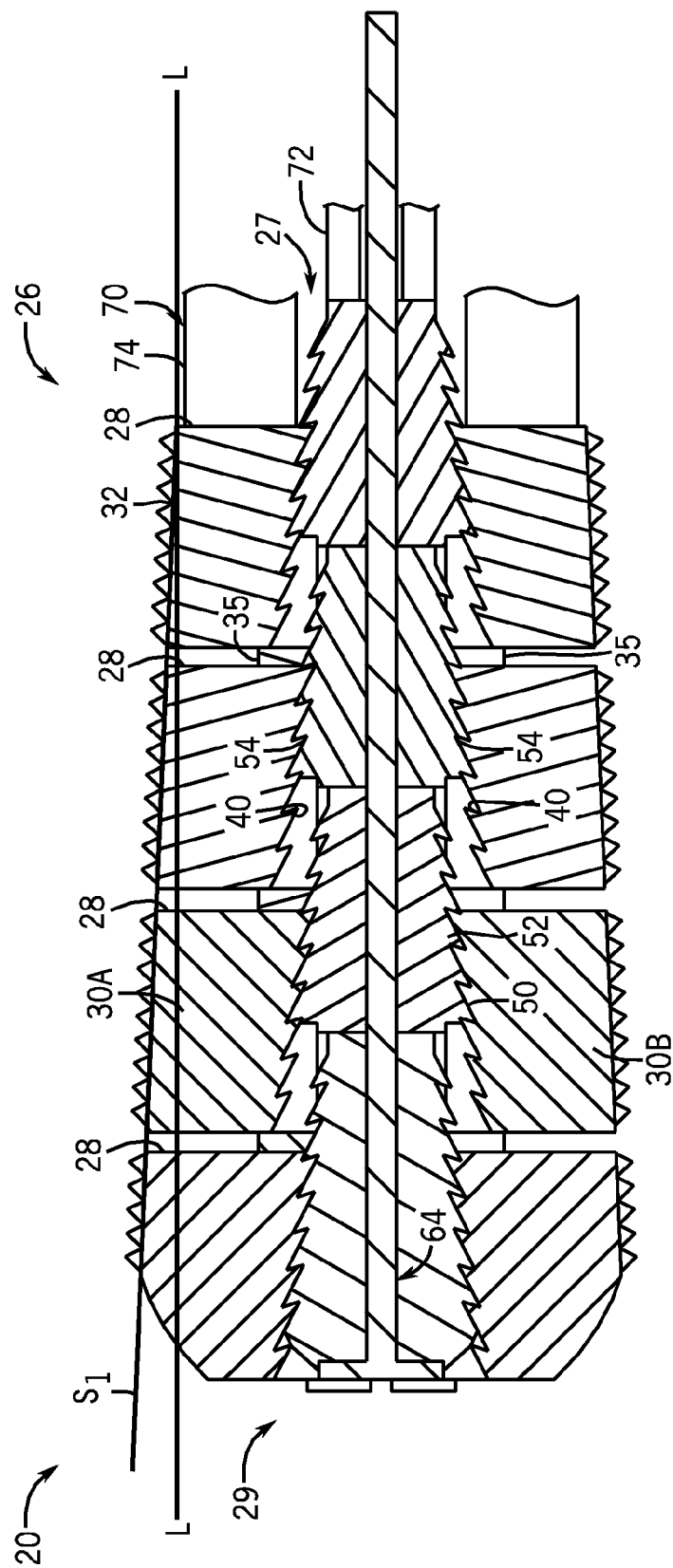
FIG. 14 is a sectional side elevation view of an expandable intervertebral implant similar to FIG. 10, but configured to define a lordotic outer profile when expanded, in accordance with an alternative embodiment.

Alternatively or additionally, the expandable intervertebral implant 20 can include an auxiliary retainer such as a flexible band 100 as illustrated in FIG. 13. The band 100 defines a body 101 that extends generally in the longitudinal direction, and defines a pair of opposing terminal ends 102 that each define connection locations that can be connected to an outer sleeve portion 30A or 30B of a different one of the plurality of links 28. The terminal ends 102 can define a hinged connection with respect to the outer sleeve portion, or can define a fixed connection such that the flexibility of the band 100 allows the terminal ends 102 and other connection locations to rotate relative to the body 101. The bands 100 can be fastened to the outer sleeve portions 30A and 30B using any suitable mechanical fastener.

In the illustrated embodiment, the terminal ends 102 of one band 100 are connected to the laterally outer surfaces of the upper sleeve portions 30A of the longitudinally outermost links 28. The terminal ends 102 of another band 100 are connected to the laterally outer surfaces of the lower sleeve portions 30B of the longitudinally outermost links 28. A pair of substantially identical bands can be connected to the opposing outer lateral surfaces of the upper and lower sleeve portions 30A and 30B. Thus, the bands 100 provide a longitudinal compressive force to all links 28 disposed between the terminal band ends 102. Alternatively, the bands 100 can be connected to one or more, up to all, links 28 that are disposed between the terminal ends 102 of the bands 100.

It should be appreciated that FIGS. 10-13 illustrate the intervertebral implant 20 configured to produce a lordotic profile in accordance with one embodiment, and that alternative embodiments can be provided to create a lordotic profile. For instance, referring to FIG. 13, the vertebral engagement surfaces 32 of each outer sleeve portions 30A and 30B are aligned with the vertebral engagement surfaces 32 of the corresponding outer sleeve portions 30A and 30B of the adjacent links. Thus, the vertebral engagement surfaces 32 of each outer sleeve portion 30A are aligned and parallel to each other, and the vertebral engagement surfaces 32 of each outer sleeve portion 30b are aligned and parallel to each other. Moreover, the engagement surfaces 32 of each outer sleeve portion 30A and 30B can be sloped with respect to the longitudinal axis L-L. In the illustrated embodiment, the engagement surfaces 32 define a slope $S_1$ that is angled transversely out from the longitudinal axis L-L in a direction from the front end 27 of the linkage 26 toward the rear end of the linkage. It should be appreciated, however, that the engagement surfaces 32 could alternatively slope transversely in from the longitudinal axis L-L in a direction from the front end 27 of the linkage 26 toward the rear end of the linkage.

Furthermore, the engagement surfaces 40 and 50 of each outer sleeve portion 30A are aligned with and extend parallel to the engagement surfaces 40 and 50 of the outer sleeve portions 30A of the other links 28. Likewise, the engagement surfaces 40 and 50 of each outer sleeve portion 30B are aligned with and extend parallel to the engagement surfaces 40 and 50 of the outer sleeve portions 30B of the other links 28. Accordingly, as the implant is expanded to the expanded position illustrated in FIG. 13, each link 28 is displaced transversely outward at the same displacement rate of the other links, and the vertebral engaging surfaces 32 maintain the lordotic profile described above.

Thus, the expandable intervertebral implant 20 is configured to expand along the transverse direction and can be further configured such that the vertebral engaging surfaces 32 can define a lordotic profile when engaged with the vertebrae. Alternatively or additionally, the intervertebral implant 20 can be configured such that the vertebral engaging surfaces 32 of the links 28 combine to define a nonlinear shape, such as a curved convex shape having outer longitudinal ends that are disposed transversely inward with respect to a longitudinal middle portion.

Figure 15A:
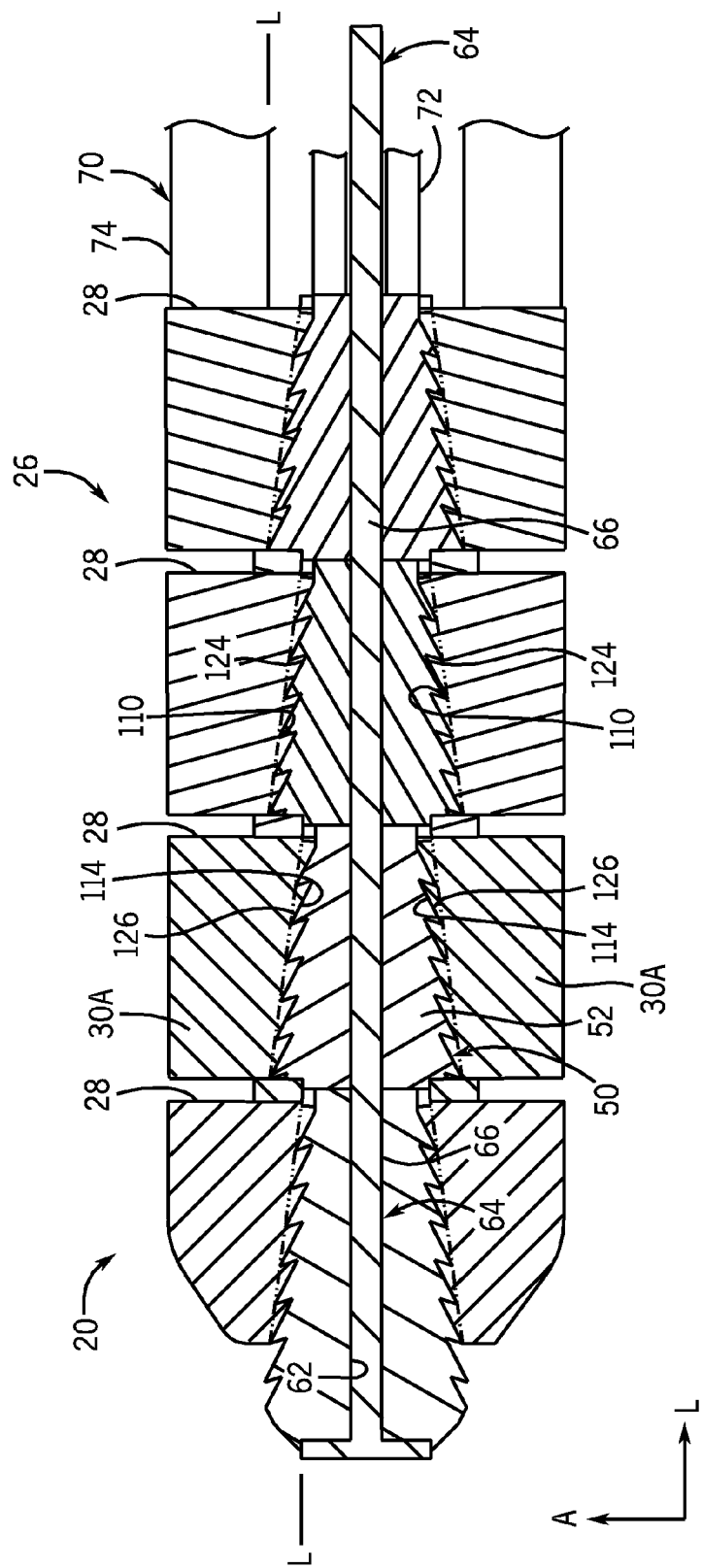
FIG. 15A is a top sectional view of an expandable intervertebral implant similar to that illustrated in FIG. 6, but further configured for lateral expansion in accordance with an alternative embodiment, wherein the expandable intervertebral implant is shown in a laterally contracted position.

Referring to FIG. 15A, the opposing axially inner surfaces of the legs 33 of each outer sleeve portion 30A and 30B can define laterally opposing, and vertically extending, engagement surfaces 110 that can be longitudinally elongate, and sloped laterally with respect to the longitudinal axis L-L at any desired angle as described above with respect to the transverse angle formed between inner engagement surface 40 and the longitudinal axis. Accordingly, that the engagement surface 110 of each sleeve portion slopes laterally out from the longitudinal axis along a direction from the front end 27 toward the rear end 29 of the linkage 26. In this regard, it should be appreciated that the laterally sloped engagement surface 110 can be constructed as described above with respect to the transversely sloped engagement surface 40. However, the cross beam 31 of each outer annular sleeve is discontinuous along the lateral direction, such that each leg the outer sleeve portions 30A and 30B is free to move relative to the other leg of same outer sleeve portion in the lateral direction. Each leg of a given outer sleeve portion is free to move in the transverse direction with respect to the legs of the opposing outer sleeve portion in the manner described above.

The engagement surfaces 110 of the upper sleeve portions 30A can define an angle greater or less than that of the other, and can further define an angle greater or less than that of the engagement surfaces 110 of the lower sleeve portions 30B, thereby causing one lateral side of the outer sleeve 30 to expand laterally at a higher or lower expansion rate, respectively, relative to the other lateral side of the outer sleeve 30. In this regard, it should be appreciated that the angle of one or both of the of the inner engagement surfaces 110 relative to the longitudinal axis L-L could be zero, while the angle of the other engagement surface 110 relative to the longitudinal axis L-L is non-zero, thereby causing only one lateral side of the outer sleeve to expand laterally during operation.

The engagement surfaces 110 of each link 28 can be aligned with, and extend parallel to, the engagement surfaces 110 of the other links 28 of the linkage 26. Thus, the outer sleeve 30 of each link 28 can extend laterally at its front end a greater amount than at its rear end. Each link 28 can further include an engagement member in the form of reverse angled teeth 114 that project laterally inward from the engagement surface 110. The lateral teeth 114 can be constructed in the manner described above with reference to the transverse teeth 44.

The inner core body 52 defines laterally outer engagement surfaces 124 that are configured to engage the engagement surfaces 110 of the upper and lower sleeves 30A and 30B. The inner core body 52 can extend vertically a sufficient distance such that each engagement surface 124 can engage with the pair of complementary engagement surfaces 110 on each lateral side of the sleeve 30. The engagement surfaces 124 can be laterally sloped with respect to the longitudinal axis L-L, and can thus extend parallel to the corresponding engagement surfaces 110. The lateral engagement surfaces 124 can be constructed as described above with respect to the transverse engagement surfaces 54. The inner core 50 can further include an engagement member in the form of reverse angled teeth 126 that project laterally out from the engagement surfaces 124. The teeth 126 can be sized and shaped substantially identical with respect to teeth 114, so as to mate with teeth 114. The teeth 126 can be constructed in the manner described above with respect to teeth 56.

Figure 15B:
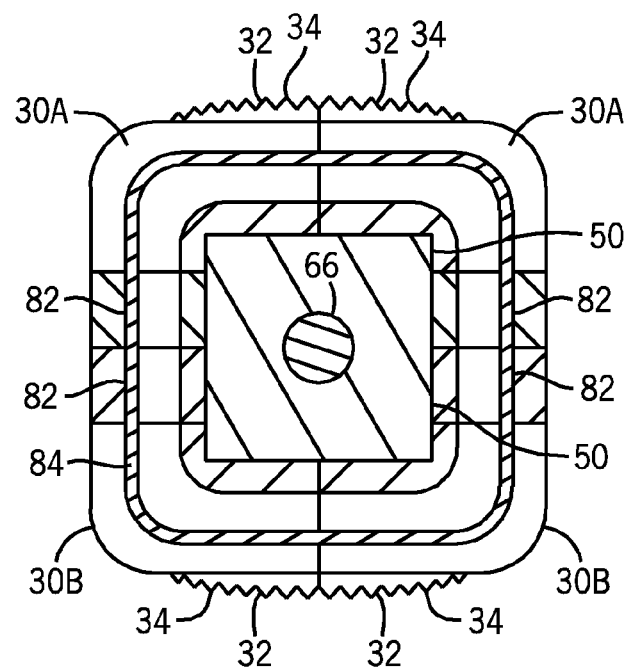
FIG. 15B is a sectional end view of the expandable intervertebral implant illustrated in FIG. 15A including a retainer constructed in accordance with one embodiment.

As illustrated in FIG. 15B, the outer sleeve portions 30A and 30B can be retained by a retainer such as a plurality of bands 84 in the manner described above. Slots 82 can extend vertically through both pairs of opposing laterally outer legs 33, and the band 84 can be inserted into the slots 82 and placed in the groove 86 in the manner described above to apply compressive retention forces onto the linkage, thereby assisting in securing the structural integrity of the expandable intervertebral implant 20. Alternatively, as illustrated in FIG. 15D, the retainer may be provided as an elasticized band 88 that is placed in the groove 86 in the manner described above to apply laterally and transverse compressive securing forces.

Figure 15C:
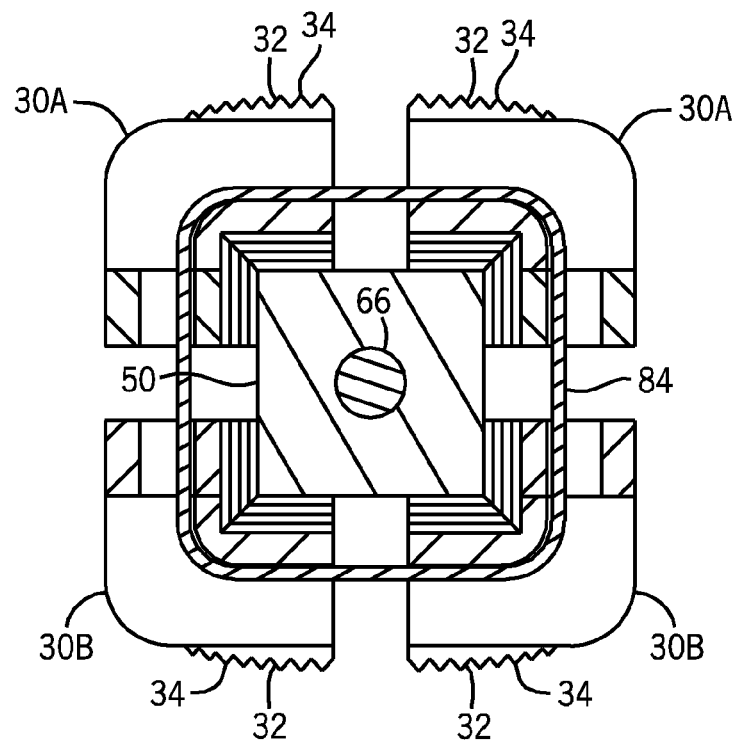
FIG. 15C is a sectional end view of the expandable intervertebral implant similar to FIG. 15B, but showing the expandable intervertebral implant in a vertically and laterally expanded position.
Figure 15D:
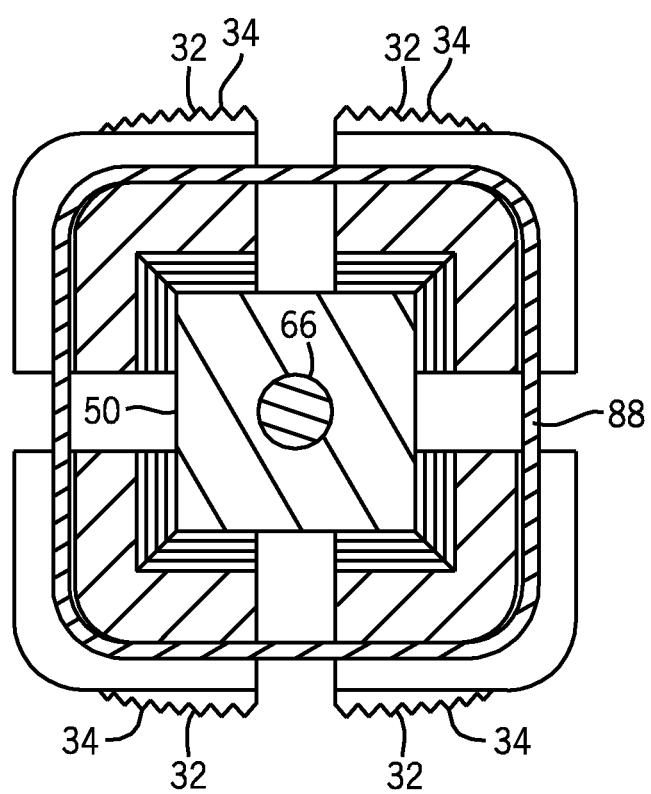
FIG. 15D is a sectional end view of the expandable intervertebral implant similar to FIG. 15C, but including a retainer constructed in accordance with an alternative embodiment.

Referring now to FIGS. 15A and 15C, as the inner core 50 moves in the forward direction with respect to the outer sleeve 30, the engagement surfaces 40 ride along the complementary engagement surfaces 54, and the teeth 44 and 56 cam over each other, thereby causing the outer sleeve portions 30A and 30B to incrementally deflect vertically away from each other in the manner described above. Furthermore, the engagement surfaces 110 ride along the complementary engagement surfaces 124, and the teeth 114 and 126 cam over each other, thereby causing the laterally outer portions of the outer sleeve 30 to incrementally deflect laterally away from each other from a first laterally contracted position to a second laterally expanded position. It should be appreciated that the engagement surfaces 110 and 124 can have a slope that is greater than or less than the slope of engagement surfaces 40 and 54, such that the implant 20 can expand vertically at a greater rate or a lesser rate than the implant 20 expands laterally.

It should be appreciated that a kit can be provided that includes all or a portion of the expandable intervertebral implant 20 constructed in accordance with any of the embodiments described herein. For example, the kit can include one or more of the components of the expandable intervertebral implant, such as the upper and lower outer sleeve portions 30A and 30B, the inner core 50, bands 84 and 88, and a plurality of links 28. The one or more components included in various kits can have one or more varying characteristic such as size and/or shape. For instance, a first kit can be provided having one or more components, for instance outer sleeve portions 30A and 30B, the inner core 50, bands 84 and 88, and a plurality of links 28, that have a different size or shape to accommodate different expansion rates, different longitudinal and/or lateral lengths, and different directions of expansion, for instance transverse expansion alone or coupled with lateral expansion. Some components in a given kit may permit the implant 20 to produce a lordotic profile in the manner described above, while other components in the kit may permit the implant to produce a horizontal upper and lower vertebrae-engaging surface. The kit can further include components of the insertion tool 70 as will now be described.

In particular, referring now to FIGS. 16A-C, the insertion tool 70 can be configured to engage the intervertebral implant 20 such that the implant 20 may be inserted into the intervertebral space 22 and subsequently expanded in the manner described above. Once the intervertebral implant is disposed in the intervertebral space, the insertion tool can include biasing members that apply a biasing force to the implant, thereby causing the implant to expand in any manner as described above. Once the implant 20 has reached the desired expansion position, the insertion tool 70 may be disengaged from the implant 20.

The insertion tool 70 can include the inner annular holding sleeve 72, the biasing member 64 that extends inside the inner annular holding sleeve 72, and the outer annular holding sleeve 74 that receives the inner annular holding sleeve 72. Once the holding member 70 is moved to position such that the inner annular holding sleeve 72 abuts the inner core 50 and the outer annular holding sleeve 74 abuts the outer sleeve 30, a force F1 can be applied to the wire 66 that causes the implant to expand in the manner described above.

Figure 17A:
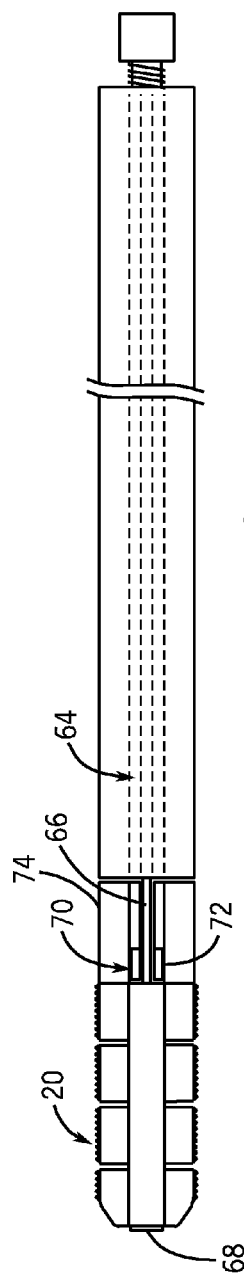
FIG. 17A is a side elevation view of the expandable intervertebral implant as illustrated in FIG. 16C, but showing the insertion device including a central sleeve having a coupling member that locks the insertion device in the engaged configuration.
Figure 17B:
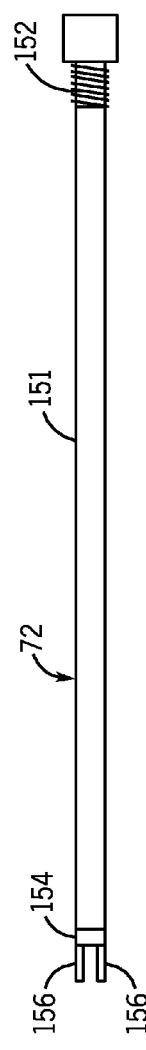
FIG. 17B is a side elevation view of the central sleeve illustrated in FIG. 17A.
Figure 17C:
FIG. 17C is a top plan view of the central sleeve illustrated in FIG. 17B.

Referring to FIGS. 17A-C, the inner annular holding sleeve 72 can include a longitudinally elongate body 151 having a threaded engagement surface 152 at a distal end that is configured to be threadedly received in the outer annular holding sleeve 74. The inner annular holding sleeve 72 can include a proximal end having a forked abutment member 154. The forked abutment member 154 can include a pair of spaced prongs 156 that are configured to abut the inner core 50 in the manner described above. The wire 62 can thus extend through the inner core 50 of each link 28, between the prongs 156 and through the inner annular holding sleeve 72. The free end of the wire that extends through the inner annular holding sleeve can be coupled to any suitable tensioning device configured to apply a biasing force sufficient to cause the intervertebral implant 20 to expand.

Referring now to FIGS. 18A-B, the insertion tool 70 can further include an angulated member 158 that is connected between the forward end 127 of the linkage 26, and the proximal ends of the inner and outer holding sleeves 72 and 74. The angulated member 158 can include a rectangular block 159, a cylindrical body 160 rigidly attached to the block 159, and a bore 162 extending through the body 160 sized to receive the wire 66. The wire 66 can thus extend through the linkage 56, the cylindrical body 160, and the inner sleeve 72. The outer sleeve 73 can define a bore 164 extending longitudinally therethrough, and a directional rod 166 extending through the bore 164. The directional rod 166 defines a proximal end that is pivotally coupled to the block 159 at a connection location 158 that is laterally offset with respect to the lateral center of the cylindrical body 160.

During operation, the rectangular block 159 abuts the inner core 50, and the directional rod 166 can be moved longitudinally forward and rearward, thereby causing the cylindrical body 160 to rotate relative to the proximal ends of the inner and outer sleeves 72 and 74. As the cylindrical body 160 rotates, the rectangular block 159 causes the intervertebral implant to change its angular orientation in the horizontal plane defined by the lateral and longitudinal directions. As illustrated, movement of the rod 166 in a forward direction causes the intervertebral implant 20 to pivot in a clockwise direction, while movement of the rod 166 in a rearward direction causes the implant to pivot in a counterclockwise direction. It should be appreciated, of course, that the rod 166 could alternatively be connected to the rectangular block 159 at a location that causes the intervertebral implant 20 to pivot in the clockwise direction when the rod is moved rearward, and counterclockwise when the rod is moved forward.

During operation, the longitudinal position of the rod 166 can be determined prior to inserting the intervertebral implant 20 into the disc space 22 so as to define an angular orientation of the implant 20 relative to the inner and outer sleeves 72 and 74. The angular orientation of the implant 20 allows the implant to be inserted into the body cavity along an anteroposterior directional approach or a posterior-anterior directional approach, while at the same time orienting the implant such that the longitudinal axis L defines a desired angle with respect to the anterior and posterior directions when the implant is inserted into the disc space 22. Once the intervertebral implant 20 has been inserted into the disc space 22, the wire 66 can be moved longitudinally forward to cause the implant 20 to expand in the transverse direction T alone, or in the transverse direction T and simultaneously the lateral direction A. Moreover, as the implant 20 expands in either the transverse direction T alone or in the transverse direction T simultaneously with the lateral direction A, the opposing transverse vertebral-engaging surfaces 32 can remain flat and parallel with each other, or can define an angular orientation configured to restore lordosis to the vertebrae 24 in the manner described above.

Figure 19A:
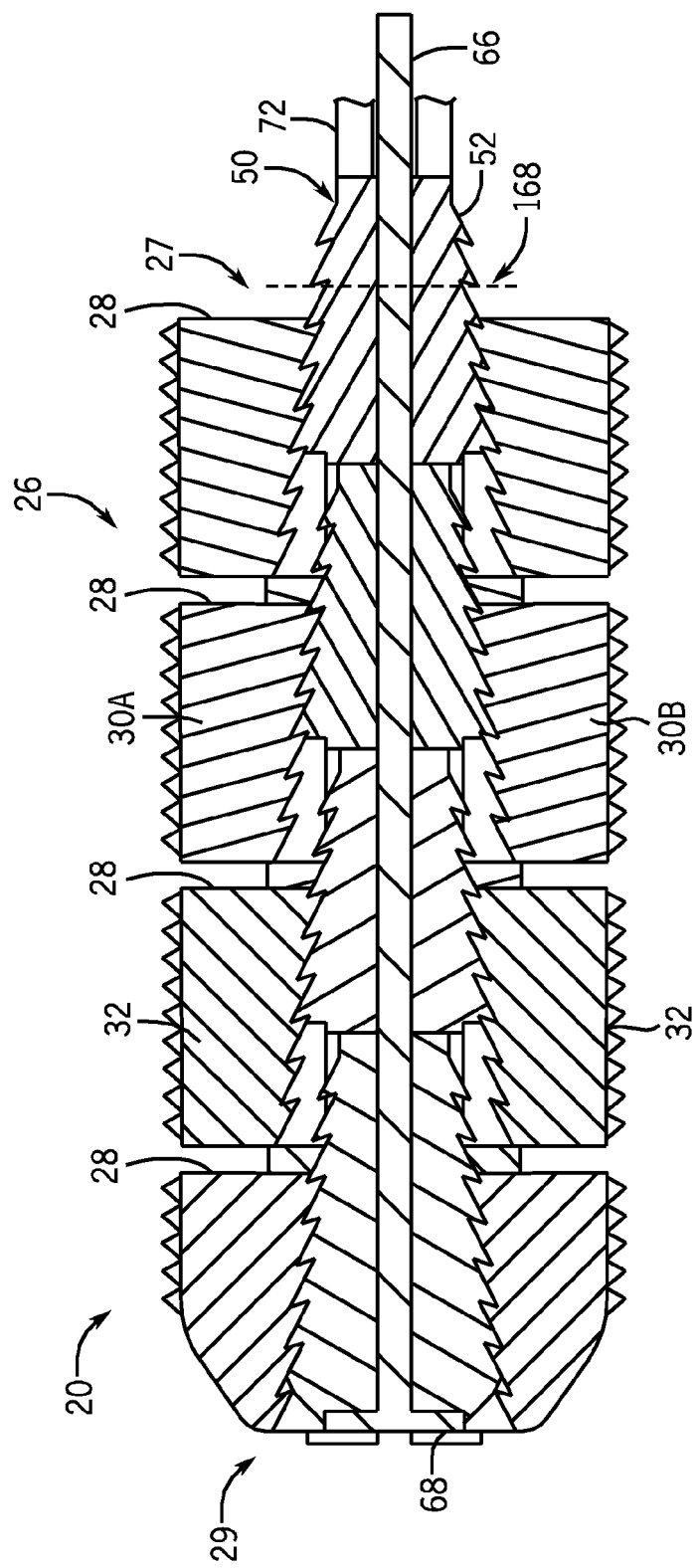
FIG. 19A is a sectional side elevation view of an expandable intervertebral implant shown in an expanded position.
Figure 19B:
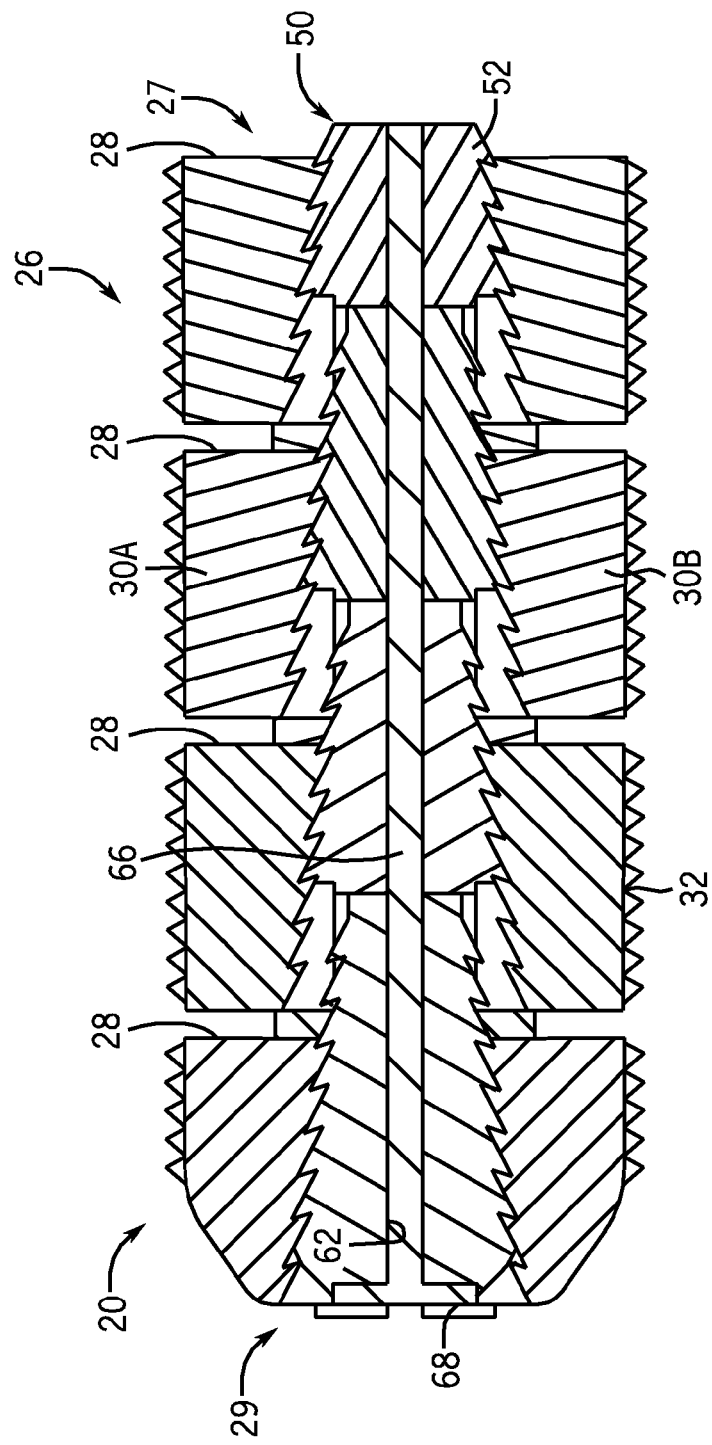
FIG. 19B is a sectional side elevation view of the expandable intervertebral implant illustrated in FIG. 19A, but showing projecting portions removed after the implant has achieved the final expanded position.

Finally, referring to FIGS. 19A and 19B, once the implant 20 has been positioned in the intervertebral space 22 and expanded to the desired expanded position, the outer sleeve 72 can be removed out of engagement with the intervertebral implant, and the remaining portions of the tool 70 can be removed by cutting the portion of the intervertebral body 50 that protrudes the front end 127 of the linkage 26 along a cut line 168 along the lateral-transverse plane LT. The cut can be made in from opposing directions, for instance using reciprocal blades at opposing locations, such that the blades can cut through the inner core body 52 and the wire 66 and cause the body 50 to crimp around the wire 66. Alternatively, the inner core body 52 can be cut in any desired manner, and a separate crimping tool can be used to crimp the body 50 around the wire 66 after the body 50 and wire 66 have been cut, thereby securing the wire and preventing the wire 66 from being inadvertently removed after the surgical procedure has been completed.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed:

1. An expandable intervertebral implant insertable into an intervertebral disc space disposed between a lower vertebra and an upper vertebra, the expandable intervertebral implant comprising:

a rear end that defines a guide surface for insertion into the intervertebral disc space, and a front end opposite the rear end, wherein the front and rear ends are spaced from each other along a longitudinal axis, such that the front end is spaced away from the rear end along the longitudinal axis;

an outer sleeve including an upper sleeve portion that defines an upper vertebral engagement surface configured to abut the upper vertebra when the implant is disposed in the intervertebral disc space, the outer sleeve further including a lower sleeve portion that defines a lower vertebral engagement surface that is spaced from the upper vertebral engagement surface and is configured to abut the lower vertebra when the implant is disposed in the intervertebral disc space, wherein 1) the upper sleeve portion defines respective first and second engagement surfaces, and 2) the outer sleeve defines an internal void at a location between the upper vertebral engagement surface and the lower vertebral engagement surface; and an inner core including respective first and second core engagement surfaces, one of the first and second core engagement surfaces spaced in its entirety from the other of the first and second core engagement surfaces in a direction away from the rear end along the longitudinal axis, the first and second core engagement surfaces configured to engage the first and second engagement surfaces, respectively, of the upper sleeve portion, such that translation of the inner core in the direction away from the rear end along the longitudinal axis in the internal void causes the first and second core engagement surfaces of the inner core to move together along the first and second engagement surfaces of the upper sleeve portion in the direction away from the rear end along the longitudinal axis, thereby causing the first and second engagement surfaces of the upper sleeve portion to ride along respective ones of the first and second core engagement surfaces of the inner core, which in turn urges an entirety of the upper sleeve portion to move away from an entirety of the lower sleeve portion along a transverse direction that is perpendicular to the longitudinal axis so as expand the implant from an initial position to an expanded position, whereby 1) in the initial position, the upper and lower vertebral engagement surfaces are spaced from each other a first distance, and 2) in the expanded position, a) the upper and lower vertebral engagement surfaces are spaced from each other a second distance greater than the first distance, and b) the first and second core engagement surfaces of the inner core remain in contact with the first and second engagement surfaces of the upper sleeve portion, wherein when the implant is in the expanded position, the implant is configured to prevent the upper and lower sleeve portions from moving toward each other so as to decrease the second distance, and wherein the first and second core engagement surfaces of the inner core are each sloped in the direction away from the rear end along the longitudinal axis as they extend away from the upper vertebral engagement surface, and the first and second engagement surfaces of the upper sleeve portion are each sloped in the direction away from the rear end along the longitudinal axis as they extend away from the upper vertebral engagement surface.

2. The expandable intervertebral implant as recited in claim 1, wherein the first and second core engagement surfaces of the inner core are parallel to each other and the first and second engagement surfaces of the upper sleeve portion.

3. The expandable intervertebral implant as recited in claim 1, wherein the first and second engagement surfaces of the upper sleeve portion are parallel to each other.

4. The expandable intervertebral implant as recited in claim 1, wherein the first and second core engagement surfaces of the inner core are parallel to each other.

5. The expandable intervertebral implant as recited in claim 1, wherein:

the lower sleeve portion defines respective third and fourth engagement surfaces each sloped in the direction away from the rear end along the longitudinal axis as they extend away from the lower vertebral engagement surface, the inner core defines respective third and fourth core engagement surfaces, and translation of the inner core in the direction away from the rear end along the longitudinal axis in the internal void further causes the third and fourth engagement surfaces of the lower sleeve portion to ride along respective ones of the third and fourth core engagement surfaces of the inner core, thereby causing the entirety of the lower sleeve portion to move away from the entirety of the upper sleeve portion along the transverse direction.

6. The expandable intervertebral implant as recited in claim 5, wherein the first and second core engagement surfaces of the inner core are parallel to the first and second engagement surfaces of the upper sleeve portion, and the third and fourth core engagement surfaces of the inner core are parallel to the third and fourth engagement surfaces of the lower sleeve portion.

7. The expandable intervertebral implant as recited in claim 1, wherein the rear end is tapered.

8. An expandable intervertebral implant insertable into an intervertebral disc space disposed between a lower vertebra and an upper vertebra, the expandable intervertebral implant comprising:

a rear end that defines a guide surface for insertion into the intervertebral disc space, and a front end opposite the rear end, wherein the front and rear ends are spaced from each other along a longitudinal axis, such that the front end is spaced away from the rear end along the longitudinal axis;

an outer sleeve including an upper sleeve portion that defines an upper vertebral engagement surface configured to abut the upper vertebra when the implant is disposed in the intervertebral disc space, the outer sleeve further including a lower sleeve portion that defines a lower vertebral engagement surface that is spaced from the upper vertebral engagement surface and is configured to abut the lower vertebra when the implant is disposed in the intervertebral disc space, wherein 1) the lower sleeve portion defines respective first and second engagement surfaces, and 2) the outer sleeve defines an internal void at a location between the upper vertebral engagement surface and the lower vertebral engagement surface; and an inner core including respective first and second core engagement surfaces, one of the first and second core engagement surfaces spaced from the other of the first and second core engagement surfaces in its entirety in a direction away from the rear end along the longitudinal axis, the first and second core engagement surfaces configured to engage the first and second engagement surfaces, respectively, of the lower sleeve portion, such that translation of the inner core in the direction away from the rear end along the longitudinal axis in the internal void causes the first and second core engagement surfaces of the inner core to move together in the direction away from the rear end along the longitudinal axis along the first and second engagement surfaces of the lower sleeve portion, thereby causing the first and second engagement surfaces of the lower sleeve portion to ride along respective ones of the first and second core engagement surfaces of the inner core, which in turn urges an entirety of the lower sleeve portion to move away from an entirety of the upper sleeve portion along a transverse direction that is perpendicular to the longitudinal axis so as expand the implant from an initial position to an expanded position, whereby 1) in the initial position, the upper and lower vertebral engagement surfaces are spaced from each other a first distance, and 2) in the expanded position, a) the upper and lower vertebral engagement surfaces are spaced from each other a second distance greater than the first distance, and b) the first and second core engagement surfaces of the inner core remain in contact with the first and second engagement surfaces of the lower sleeve portion, wherein when the implant is in the expanded position, the implant is configured to prevent the upper and lower sleeve portions from moving toward each other so as to decrease the second distance, and wherein the first and second core engagement surfaces of the inner core are each sloped in the direction away from the rear end along the longitudinal axis as they extend away from the lower vertebral engagement surface, and the first and second engagement surfaces of the lower sleeve portion are each sloped in the direction away from the rear end along the longitudinal axis as they extend away from the lower vertebral engagement surface.

9. The expandable intervertebral implant as recited in claim 8, wherein the first and second core engagement surfaces of the inner core are parallel to the first and second engagement surfaces of the lower sleeve portion.

10. The expandable intervertebral implant as recited in claim 8, wherein the first and second engagement surfaces of the lower sleeve portion are parallel to each other.

11. The expandable intervertebral implant as recited in claim 8, wherein the first and second core engagement surfaces of the inner core are parallel to each other.

12. An expandable intervertebral implant insertable into an intervertebral disc space disposed between a lower vertebra and an upper vertebra, the expandable intervertebral implant comprising:
  a rear end that defines a guide surface for insertion into the intervertebral disc space, and a front end opposite the rear end along a longitudinal axis, wherein the front end is spaced away from the rear end along the longitudinal axis;
  an outer sleeve that includes;
    an upper sleeve portion including an upper cross beam and a pair of upper legs that each project down from the upper cross beam, wherein the upper cross beam defines an upper vertebral engagement surface configured to abut the upper vertebra when the implant is disposed in the intervertebral disc space, and
    a lower sleeve portion including a lower cross beam and a pair of lower legs that each project up from the lower cross beam, wherein the lower cross beam defines a lower vertebral engagement surface configured to abut the lower vertebra when the implant is disposed in the intervertebral disc space,
    wherein the outer sleeve defines an internal void at a location between the upper vertebral engagement surface and the lower vertebral engagement surface; and
  an inner core including first and second core engagement surfaces, one of the first and second core engagement surfaces spaced in its entirety from the other of the first and second core engagement surfaces in a direction away from the rear end along the longitudinal axis, the first and second core engagement surfaces configured to engage engagement surfaces of the outer sleeve, such that translation of the inner core in the direction away from the rear end along the longitudinal axis in the internal void causes the first and second core engagement surfaces to move together in the direction away from the rear end along the longitudinal axis along the engagement surfaces of the outer sleeve, thereby causing an entirety of each of the upper and lower sleeve portions to move away from an entirety of the other of the upper and lower sleeve portions so as expand the implant from an initial position to an expanded position, whereby 1) in the initial position, a) the upper and lower vertebral engagement surfaces are spaced from each other a first distance, and b) the legs of the pair of upper legs abut respective ones of the legs of the pair of lower legs, and 2) in the expanded position, a) the upper and lower vertebral engagement surfaces are spaced from each other a second distance greater than the first distance, and b) the first and second core engagement surfaces remain in contact with the engagement surfaces of the outer sleeve,
  wherein when the implant is in the expanded position, the implant is configured to prevent the upper and lower sleeve portions from moving toward each other so as to decrease the second distance.

13. The expandable intervertebral implant as recited in claim 12, wherein the legs of the pair of upper legs are spaced from respective ones of the legs of the pair of lower legs when the implant is in the expanded position.

14. An expandable intervertebral implant insertable into an intervertebral disc space disposed between a lower vertebra and an upper vertebra, the expandable intervertebral implant comprising:
  a rear end that defines a guide surface for insertion into the intervertebral disc space, and a front end spaced away from the rear end along a longitudinal axis;
  an upper sleeve portion that defines an upper vertebral engagement surface configured to abut the upper vertebra when the implant is disposed in the intervertebral disc space, the upper sleeve portion defining respective first and second engagement surfaces each sloped in a direction away from the rear end along the longitudinal axis as they extend away from the upper vertebral engagement surface;
  a lower sleeve portion that defines a lower vertebral engagement surface configured to abut the lower vertebra when the implant is disposed in the intervertebral disc space, the lower sleeve portion defining respective third and fourth engagement surfaces each sloped in the direction away from the rear end along the longitudinal axis as they extend away from the lower vertebral engagement surface; and
  an inner core translatable in the direction away from the rear end along the longitudinal axis with respect to each of the upper and lower sleeve portions at a location between the upper and lower vertebral engagement surfaces, the inner core defining 1) respective first and second core engagement surfaces that are each sloped in the direction away from the rear end along the longitudinal axis as they extend away from the upper vertebral engagement surface, and 2) respective third and fourth core engagement surfaces each sloped in the direction away from the rear end along the longitudinal axis as they extend away from the lower vertebral engagement surface,
  wherein translation of the inner core in the direction away from the rear end along the longitudinal axis with respect to each of the upper and lower sleeve portions causes the implant to expand from an initial position to an expanded position, whereby 1) the first and second core engagement surfaces of the inner core translate together in the direction away from the rear end along the longitudinal axis with respect to each of the upper and lower sleeve portions, thereby causing the first and second engagement surfaces of the upper sleeve portion to ride along respective ones of the first and second core engagement surfaces of the inner core, which causes an entirety of the upper sleeve portion to move away from an entirety of the lower sleeve portion, and 2) the third and fourth core engagement surfaces of the inner core translate together in the direction away from the rear end along the longitudinal axis with respect to each of the upper and lower sleeve portions, thereby causing the third and fourth engagement surfaces of the lower sleeve portion to ride along respective ones of the third and fourth core engagement surfaces of the inner core, which causes an entirety of the lower sleeve portion to move away from an entirety of the upper sleeve portion, whereby 1) in the initial position, the upper and lower vertebral engagement surfaces are spaced from each other a first distance, and 2) in the expanded position, the upper and lower vertebral engagement surfaces are spaced from each other a second distance greater than the first distance while a) the first and second core engagement surfaces are in contact with the first and second engagement surfaces, respectively, of the upper sleeve portion, and b) the third and fourth core engagement surfaces are in contact with the third and fourth engagement surfaces, respectively, of the lower sleeve portion, wherein when the implant is in the expanded position, the implant is configured to prevent the upper and lower sleeve portions from moving toward each other so as to reduce the second distance.

15. The expandable intervertebral implant as recited in claim 14, wherein the rear end is tapered.

16. The expandable intervertebral implant as recited in claim 14, wherein:

the upper sleeve portion comprises an upper cross beam and a pair of upper legs that each project down from the upper cross beam, the lower sleeve portion comprises a lower cross beam and a pair of lower legs that each project up from the lower cross beam, and the legs of the pair of upper legs abut respective ones of the legs of the pair of lower legs when the implant is in the initial position.

17. The expandable intervertebral implant as recited in claim 16, wherein the upper legs are spaced from the lower legs when the implant is in the expanded position.

\* \* \* \* \*